US012029545B2

(12) United States Patent
Bar-Tal et al.

(10) Patent No.: US 12,029,545 B2
(45) Date of Patent: Jul. 9, 2024

(54) CATHETER SPLINES AS LOCATION SENSORS

(71) Applicant: Biosense Webster (Israel) Ltd., Yokneam (IL)

(72) Inventors: Meir Bar-Tal, Haifa (IL); Avram Dan Montag, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 1225 days.

(21) Appl. No.: 15/971,966

(22) Filed: May 4, 2018

(65) Prior Publication Data

US 2018/0344202 A1 Dec. 6, 2018

Related U.S. Application Data

(60) Provisional application No. 62/512,263, filed on May 30, 2017.

(51) Int. Cl.
*A61B 5/06* (2006.01)
*A61B 5/00* (2006.01)
(Continued)

(52) U.S. Cl.
CPC .............. *A61B 5/062* (2013.01); *A61B 5/287* (2021.01); *A61B 5/341* (2021.01); *A61B 5/6853* (2013.01);
(Continued)

(58) Field of Classification Search
CPC ......... A61B 5/062; A61B 34/20; A61B 90/39; A61B 5/04011; A61B 5/0422;
(Continued)

(56) References Cited

U.S. PATENT DOCUMENTS

D123,782 S   12/1940   Paul
3,316,896 A   5/1967   Louis
(Continued)

FOREIGN PATENT DOCUMENTS

CN   101422637 A   5/2009
CN   102271607 A   12/2011
(Continued)

OTHER PUBLICATIONS

International Search Report dated Aug. 10, 2018, International Application No. PCT/IB2018/053633.
(Continued)

*Primary Examiner* — Ashley K Buran
*Assistant Examiner* — Helene Bor
(74) *Attorney, Agent, or Firm* — Troutman Pepper Hamilton Sanders LLP

(57) ABSTRACT

Apparatus, including a probe having a proximal end and a distal end, the probe being configured to be inserted into an organ of a human patient and defining a probe axis. At least two conductors are positioned on the probe at the distal end. The apparatus includes at least two flexible conductive splines, each conductive spline having a first termination and a second termination, the first terminations being electrically connected together at a region on the probe axis beyond the distal end, each second termination being electrically connected to a respective one of the conductors, the splines being configured to bend into respective arcuate forms that encompass a volume. The apparatus also includes a processor configured to receive voltages induced on the splines via the conductors and to calculate a position and orientation of the volume in response to the received voltages.

24 Claims, 8 Drawing Sheets

(51) Int. Cl.
  *A61B 5/01*     (2006.01)
  *A61B 5/053*    (2021.01)
  *A61B 5/287*    (2021.01)
  *A61B 5/341*    (2021.01)
  *A61B 17/00*    (2006.01)
  *A61B 18/00*    (2006.01)
  *A61B 18/14*    (2006.01)
  *A61B 34/20*    (2016.01)
  *A61B 90/00*    (2016.01)

(52) U.S. Cl.
  CPC .......... *A61B 5/6858* (2013.01); *A61B 5/6859* (2013.01); *A61B 17/00* (2013.01); *A61B 18/1492* (2013.01); *A61B 34/20* (2016.02); *A61B 90/39* (2016.02); *A61B 5/015* (2013.01); *A61B 5/053* (2013.01); *A61B 5/064* (2013.01); *A61B 2017/00053* (2013.01); *A61B 2018/0022* (2013.01); *A61B 2018/00267* (2013.01); *A61B 2018/00351* (2013.01); *A61B 2018/00577* (2013.01); *A61B 2034/2051* (2016.02); *A61B 2090/3954* (2016.02); *A61B 2560/0223* (2013.01)

(58) Field of Classification Search
  CPC ... A61B 5/6853; A61B 5/6858; A61B 5/6859; A61B 17/00; A61B 18/1492; A61B 2034/2051; A61B 2090/3954; A61B 5/015; A61B 5/053; A61B 5/064; A61B 2017/00053; A61B 2018/0022; A61B 2018/00267; A61B 2018/00351; A61B 2018/00577; A61B 2560/0223
  See application file for complete search history.

(56) References Cited

U.S. PATENT DOCUMENTS

| | | | |
|---|---|---|---|
| 4,276,874 A | 7/1981 | Wolvek et al. | |
| 4,587,975 A | 5/1986 | Salo et al. | |
| 4,699,147 A | 10/1987 | Chilson et al. | |
| 4,709,698 A | 12/1987 | Johnston et al. | |
| 4,710,708 A * | 12/1987 | Rorden .................... | G01V 3/08 |
| | | | 324/207.26 |
| 4,805,621 A | 2/1989 | Heinze et al. | |
| 4,940,064 A | 7/1990 | Desai | |
| 5,178,957 A | 1/1993 | Kolpe et al. | |
| 5,215,103 A | 6/1993 | Desai | |
| 5,255,679 A | 10/1993 | Imran | |
| 5,293,869 A | 3/1994 | Edwards et al. | |
| 5,309,910 A | 5/1994 | Edwards et al. | |
| 5,313,943 A | 5/1994 | Houser et al. | |
| 5,324,284 A | 6/1994 | Imran | |
| 5,345,936 A | 9/1994 | Pomeranz et al. | |
| 5,365,926 A | 11/1994 | Desai | |
| 5,396,887 A | 3/1995 | Imran | |
| 5,400,783 A | 3/1995 | Pomeranz et al. | |
| 5,411,025 A | 5/1995 | Webster, Jr. | |
| 5,415,166 A | 5/1995 | Imran | |
| 5,429,617 A | 7/1995 | Hammersmark et al. | |
| 5,456,254 A | 10/1995 | Pietroski et al. | |
| 5,465,717 A | 11/1995 | Imran et al. | |
| 5,476,495 A | 12/1995 | Kordis et al. | |
| 5,499,981 A | 3/1996 | Kordis | |
| 5,526,810 A | 6/1996 | Wang | |
| 5,546,940 A | 8/1996 | Panescu et al. | |
| 5,549,108 A | 8/1996 | Edwards et al. | |
| 5,553,611 A * | 9/1996 | Budd ................... | A61B 5/0422 |
| | | | 600/374 |
| 5,555,883 A * | 9/1996 | Avitall ................... | A61B 5/283 |
| | | | 600/374 |
| 5,558,073 A | 9/1996 | Pomeranz et al. | |
| 5,577,509 A | 11/1996 | Panescu et al. | |
| 5,582,609 A | 12/1996 | Swanson et al. | |
| 5,584,830 A | 12/1996 | Ladd et al. | |
| 5,595,183 A | 1/1997 | Swanson et al. | |
| 5,598,848 A | 2/1997 | Swanson et al. | |
| 5,609,157 A | 3/1997 | Panescu et al. | |
| 5,628,313 A | 5/1997 | Webster, Jr. | |
| 5,681,280 A | 10/1997 | Rusk et al. | |
| 5,702,386 A | 12/1997 | Stern et al. | |
| 5,718,241 A | 2/1998 | Ben-Haim et al. | |
| 5,722,401 A | 3/1998 | Pietroski et al. | |
| 5,722,403 A | 3/1998 | McGee et al. | |
| 5,725,525 A * | 3/1998 | Kordis .................... | A61B 5/287 |
| | | | 606/41 |
| 5,730,128 A | 3/1998 | Pomeranz et al. | |
| 5,772,590 A | 6/1998 | Webster, Jr. | |
| 5,782,899 A | 7/1998 | Imran | |
| 5,797,903 A | 8/1998 | Swanson et al. | |
| 5,823,189 A | 10/1998 | Kordis | |
| 5,860,974 A | 1/1999 | Abele | |
| 5,881,727 A | 3/1999 | Edwards | |
| 5,893,847 A | 4/1999 | Kordis | |
| 5,904,680 A | 5/1999 | Kordis et al. | |
| 5,911,739 A | 6/1999 | Kordis et al. | |
| 5,928,228 A | 7/1999 | Kordis et al. | |
| 5,968,040 A * | 10/1999 | Swanson ............ | A61B 18/1492 |
| | | | 606/41 |
| 5,971,983 A | 10/1999 | Lesh | |
| 6,012,457 A | 1/2000 | Lesh | |
| 6,014,579 A | 1/2000 | Pomeranz et al. | |
| 6,014,590 A | 1/2000 | Whayne et al. | |
| 6,024,740 A | 2/2000 | Lesh et al. | |
| 6,042,580 A | 3/2000 | Simpson | |
| 6,119,030 A | 9/2000 | Morency | |
| 6,123,718 A | 9/2000 | Tu et al. | |
| 6,164,283 A | 12/2000 | Lesh | |
| 6,171,275 B1 | 1/2001 | Webster, Jr. | |
| 6,176,832 B1 | 1/2001 | Habu et al. | |
| 6,198,974 B1 | 3/2001 | Webster, Jr. | |
| 6,216,043 B1 | 4/2001 | Swanson et al. | |
| 6,216,044 B1 | 4/2001 | Kordis | |
| 6,226,542 B1 | 5/2001 | Reisfeld | |
| 6,301,496 B1 | 10/2001 | Reisfeld | |
| 6,322,558 B1 | 11/2001 | Taylor et al. | |
| 6,380,957 B1 | 4/2002 | Banning | |
| 6,402,740 B1 | 6/2002 | Ellis et al. | |
| 6,428,537 B1 | 8/2002 | Swanson et al. | |
| D462,389 S | 9/2002 | Provence et al. | |
| 6,456,864 B1 | 9/2002 | Swanson et al. | |
| 6,471,693 B1 | 10/2002 | Carroll et al. | |
| 6,522,930 B1 | 2/2003 | Schaer et al. | |
| 6,529,756 B1 | 3/2003 | Phan et al. | |
| 6,574,492 B1 | 6/2003 | Ben-Haim et al. | |
| 6,584,345 B2 | 6/2003 | Govari | |
| 6,600,948 B2 | 7/2003 | Ben-Haim et al. | |
| 6,656,174 B1 | 12/2003 | Hegde et al. | |
| 6,738,655 B1 | 5/2004 | Sen et al. | |
| 6,741,878 B2 | 5/2004 | Fuimaono et al. | |
| 6,748,255 B2 | 6/2004 | Fuimaono et al. | |
| 6,780,183 B2 | 8/2004 | Jimenez, Jr. et al. | |
| 6,814,733 B2 | 11/2004 | Schwartz et al. | |
| 6,837,886 B2 | 1/2005 | Collins et al. | |
| 6,866,662 B2 | 3/2005 | Fuimaono et al. | |
| 6,892,091 B1 | 5/2005 | Ben-Haim et al. | |
| 6,893,433 B2 | 5/2005 | Lentz | |
| 6,893,439 B2 | 5/2005 | Fleischman | |
| 6,939,349 B2 | 9/2005 | Fleischman et al. | |
| 6,970,730 B2 | 11/2005 | Fuimaono et al. | |
| 6,973,340 B2 | 12/2005 | Fuimaono et al. | |
| 6,980,858 B2 | 12/2005 | Fuimaono et al. | |
| 6,986,744 B1 | 1/2006 | Krivitski | |
| 6,987,995 B2 | 1/2006 | Drysen | |
| 6,997,924 B2 | 2/2006 | Schwartz et al. | |
| 7,048,734 B1 | 5/2006 | Fleischman et al. | |
| 7,142,903 B2 | 11/2006 | Rodriguez et al. | |
| 7,149,563 B2 | 12/2006 | Fuimaono et al. | |
| 7,155,270 B2 | 12/2006 | Solis et al. | |
| 7,156,816 B2 | 1/2007 | Schwartz et al. | |
| 7,255,695 B2 | 8/2007 | Falwell et al. | |
| 7,257,434 B2 | 8/2007 | Fuimaono et al. | |
| 7,274,957 B2 | 9/2007 | Drysen | |

(56) References Cited

U.S. PATENT DOCUMENTS

| | | |
|---|---|---|
| 7,340,307 B2 | 3/2008 | Maguire et al. |
| 7,377,906 B2 | 5/2008 | Selkee |
| 7,399,299 B2 | 7/2008 | Daniel et al. |
| 7,410,486 B2 | 8/2008 | Fuimaono et al. |
| 7,442,190 B2 | 10/2008 | Abbound et al. |
| 7,522,950 B2 | 4/2009 | Fuimaono et al. |
| 7,536,218 B2 | 5/2009 | Govari et al. |
| 7,591,799 B2 | 9/2009 | Selkee |
| 7,593,760 B2 | 9/2009 | Rodriguez et al. |
| RE41,334 E | 5/2010 | Beatty et al. |
| 7,720,517 B2 | 5/2010 | Drysen |
| 7,756,576 B2 | 7/2010 | Levin |
| 7,842,031 B2 | 11/2010 | Abboud et al. |
| 7,846,157 B2 | 12/2010 | Kozel |
| 7,853,302 B2 | 12/2010 | Rodriguez et al. |
| 7,930,018 B2 | 4/2011 | Harlev et al. |
| 8,000,765 B2 | 8/2011 | Rodriguez et al. |
| 8,007,495 B2 | 8/2011 | McDaniel et al. |
| 8,021,327 B2 | 9/2011 | Selkee |
| 8,048,032 B2 | 11/2011 | Root et al. |
| 8,048,063 B2 | 11/2011 | Aeby et al. |
| 8,103,327 B2 | 1/2012 | Harlev et al. |
| 8,167,845 B2 | 5/2012 | Wang et al. |
| 8,224,416 B2 | 7/2012 | De La Rama et al. |
| 8,231,617 B2 | 7/2012 | Satake |
| 8,235,988 B2 | 8/2012 | Davis et al. |
| 8,267,932 B2 | 9/2012 | Baxter et al. |
| 8,275,440 B2 | 9/2012 | Rodriguez et al. |
| 8,346,339 B2 | 1/2013 | Kordis et al. |
| 8,348,888 B2 | 1/2013 | Selkee |
| 8,357,152 B2 | 1/2013 | Govari et al. |
| D682,289 S | 5/2013 | DiJulio et al. |
| D682,291 S | 5/2013 | Baek et al. |
| 8,435,232 B2 | 5/2013 | Aeby et al. |
| 8,447,377 B2 | 5/2013 | Harlev et al. |
| 8,498,686 B2 | 7/2013 | Grunewald |
| 8,517,999 B2 | 8/2013 | Pappone et al. |
| D690,318 S | 9/2013 | Kluttz et al. |
| 8,545,490 B2 | 10/2013 | Mihajlovic et al. |
| 8,560,086 B2 | 10/2013 | Just et al. |
| 8,567,265 B2 | 10/2013 | Aeby et al. |
| D694,652 S | 12/2013 | Tompkin |
| 8,641,709 B2 | 2/2014 | Sauvageau et al. |
| 8,644,902 B2 | 2/2014 | Kordis et al. |
| 8,712,550 B2 | 4/2014 | Grunewald |
| 8,721,590 B2 | 5/2014 | Seward et al. |
| 8,755,861 B2 | 6/2014 | Harlev et al. |
| 8,777,161 B2 | 7/2014 | Pollock et al. |
| 8,818,486 B2 | 8/2014 | Montag |
| 8,825,130 B2 | 9/2014 | Just et al. |
| D716,340 S | 10/2014 | Bresin et al. |
| 8,852,181 B2 | 10/2014 | Malecki et al. |
| 8,906,011 B2 | 12/2014 | Gelbart et al. |
| D720,766 S | 1/2015 | Mandal et al. |
| D721,379 S | 1/2015 | Moon et al. |
| 8,945,120 B2 | 2/2015 | McDaniel et al. |
| D724,618 S | 3/2015 | Shin |
| 8,979,839 B2 | 3/2015 | De La Rama et al. |
| 8,998,893 B2 | 4/2015 | Avitall |
| D729,263 S | 5/2015 | Ahn et al. |
| 9,037,264 B2 | 5/2015 | Just et al. |
| 9,089,350 B2 | 7/2015 | Willard |
| D736,780 S | 8/2015 | Wang |
| 9,126,023 B1 | 9/2015 | Sahatjian et al. |
| 9,131,980 B2 | 9/2015 | Bloom |
| D740,308 S | 10/2015 | Kim et al. |
| D743,424 S | 11/2015 | Danielyan et al. |
| D744,000 S | 11/2015 | Villamor et al. |
| 9,173,758 B2 | 11/2015 | Brister et al. |
| 9,204,929 B2 | 12/2015 | Solis |
| D747,742 S | 1/2016 | Fan et al. |
| D750,644 S | 3/2016 | Bhutani et al. |
| 9,277,960 B2 | 3/2016 | Weinkam et al. |
| 9,283,034 B2 | 3/2016 | Katoh et al. |
| 9,289,141 B2 | 3/2016 | Lowery et al. |
| D753,690 S | 4/2016 | Vazquez et al. |
| 9,314,208 B1 | 4/2016 | Altmann et al. |
| 9,320,631 B2 | 4/2016 | Moore et al. |
| 9,339,331 B2 | 5/2016 | Tegg et al. |
| 9,345,540 B2 | 5/2016 | Mallin et al. |
| D759,673 S | 6/2016 | Looney et al. |
| D759,675 S | 6/2016 | Looney et al. |
| D764,500 S | 8/2016 | Wang |
| D765,709 S | 9/2016 | Gagnier |
| D767,616 S | 9/2016 | Jones et al. |
| D768,696 S | 10/2016 | Gagnier |
| 9,486,282 B2 | 11/2016 | Solis |
| 9,554,718 B2 | 1/2017 | Bar-Tal et al. |
| D782,686 S | 3/2017 | Werneth et al. |
| 9,585,588 B2 | 3/2017 | Marecki et al. |
| 9,597,036 B2 | 3/2017 | Aeby et al. |
| D783,037 S | 4/2017 | Hariharan et al. |
| 9,655,677 B2 | 5/2017 | Salahieh et al. |
| 9,687,297 B2 | 6/2017 | Just et al. |
| D791,805 S | 7/2017 | Segars |
| 9,693,733 B2 | 7/2017 | Altmann et al. |
| 9,782,099 B2 | 10/2017 | Williams et al. |
| 9,788,895 B2 | 10/2017 | Solis |
| 9,795,442 B2 | 10/2017 | Salahieh et al. |
| 9,801,681 B2 | 10/2017 | Laske et al. |
| 9,814,618 B2 | 11/2017 | Nguyen et al. |
| 9,833,161 B2 | 12/2017 | Govari |
| 9,894,756 B2 | 2/2018 | Weinkam et al. |
| 9,895,073 B2 | 2/2018 | Solis |
| 9,907,609 B2 | 3/2018 | Cao et al. |
| 9,907,610 B2 | 3/2018 | Beeckler et al. |
| 9,956,035 B2 | 5/2018 | Govari et al. |
| 9,974,460 B2 | 5/2018 | Wu et al. |
| 9,986,949 B2 | 6/2018 | Govari et al. |
| 9,993,160 B2 | 6/2018 | Salvestro et al. |
| 10,014,607 B1 | 7/2018 | Govari et al. |
| 10,028,376 B2 | 7/2018 | Weinkam et al. |
| 10,034,637 B2 | 7/2018 | Harlev et al. |
| 10,039,494 B2 | 8/2018 | Altmann et al. |
| 10,045,707 B2 | 8/2018 | Govari |
| 10,078,713 B2 | 9/2018 | Auerbach et al. |
| 10,111,623 B2 | 10/2018 | Jung et al. |
| 10,130,420 B2 | 11/2018 | Basu et al. |
| 10,136,828 B2 | 11/2018 | Houben et al. |
| 10,143,394 B2 | 12/2018 | Solis |
| 10,172,536 B2 | 1/2019 | Maskara et al. |
| 10,182,762 B2 | 1/2019 | Just et al. |
| 10,194,818 B2 | 2/2019 | Williams et al. |
| 10,201,311 B2 | 2/2019 | Chou et al. |
| 10,219,860 B2 | 3/2019 | Harlev et al. |
| 10,219,861 B2 | 3/2019 | Just et al. |
| 10,231,328 B2 | 3/2019 | Weinkam et al. |
| 10,238,309 B2 | 3/2019 | Bar-Tal et al. |
| 10,278,590 B2 | 5/2019 | Salvestro et al. |
| D851,774 S | 6/2019 | Werneth et al. |
| 10,314,505 B2 | 6/2019 | Williams et al. |
| 10,314,507 B2 | 6/2019 | Govari et al. |
| 10,314,648 B2 | 6/2019 | Ge et al. |
| 10,314,649 B2 | 6/2019 | Bakos et al. |
| 10,349,855 B2 | 7/2019 | Zeidan et al. |
| 10,350,003 B2 | 7/2019 | Weinkam et al. |
| 10,362,991 B2 | 7/2019 | Tran et al. |
| 10,375,827 B2 | 8/2019 | Weinkam et al. |
| 10,376,170 B2 | 8/2019 | Quinn et al. |
| 10,376,221 B2 | 8/2019 | Iyun et al. |
| 10,398,348 B2 | 9/2019 | Osadchy et al. |
| 10,403,053 B2 | 9/2019 | Katz et al. |
| D861,717 S | 10/2019 | Brekke et al. |
| 10,441,188 B2 | 10/2019 | Katz et al. |
| 10,470,682 B2 | 11/2019 | Deno et al. |
| 10,470,714 B2 | 11/2019 | Altmann et al. |
| 10,482,198 B2 | 11/2019 | Auerbach et al. |
| 10,492,857 B2 | 12/2019 | Guggenberger et al. |
| 10,542,620 B2 | 1/2020 | Weinkam et al. |
| 10,575,743 B2 | 3/2020 | Basu et al. |
| 10,575,745 B2 | 3/2020 | Solis |
| 10,582,871 B2 | 3/2020 | Williams et al. |
| 10,582,894 B2 | 3/2020 | Ben Zrihem et al. |
| 10,596,346 B2 | 3/2020 | Aeby et al. |

(56) References Cited

U.S. PATENT DOCUMENTS

| | | |
|---|---|---|
| 10,602,947 B2 | 3/2020 | Govari et al. |
| 10,617,867 B2 | 4/2020 | Viswanathan et al. |
| 10,660,702 B2 | 5/2020 | Viswanathan et al. |
| 10,667,753 B2 | 6/2020 | Werneth et al. |
| 10,674,929 B2 | 6/2020 | Houben et al. |
| 10,681,805 B2 | 6/2020 | Weinkam et al. |
| 10,682,181 B2 | 6/2020 | Cohen et al. |
| 10,687,892 B2 | 6/2020 | Long et al. |
| 10,688,278 B2 | 6/2020 | Beeckler et al. |
| 10,702,178 B2 | 7/2020 | Dahlen et al. |
| 10,716,477 B2 | 7/2020 | Salvestro et al. |
| 10,758,304 B2 | 9/2020 | Aujla |
| 10,765,371 B2 | 9/2020 | Hayam et al. |
| 10,772,566 B2 | 9/2020 | Aujila |
| 10,799,281 B2 | 10/2020 | Goertzen et al. |
| 10,842,558 B2 | 11/2020 | Harlev et al. |
| 10,842,561 B2 | 11/2020 | Viswanathan et al. |
| 10,863,914 B2 | 12/2020 | Govari et al. |
| 10,881,376 B2 | 1/2021 | Shemesh et al. |
| 10,898,139 B2 | 1/2021 | Guta et al. |
| 10,905,329 B2 | 2/2021 | Bar-Tal et al. |
| 10,912,484 B2 | 2/2021 | Ziv-Ari et al. |
| 10,918,306 B2 | 2/2021 | Govari et al. |
| 10,939,871 B2 | 3/2021 | Altmann et al. |
| 10,952,795 B2 | 3/2021 | Cohen et al. |
| 10,973,426 B2 | 4/2021 | Williams et al. |
| 10,973,461 B2 | 4/2021 | Baram et al. |
| 10,987,045 B2 | 4/2021 | Basu et al. |
| 11,006,902 B1 | 5/2021 | Bonyak et al. |
| 11,040,208 B1 | 6/2021 | Govari et al. |
| 11,045,628 B2 | 6/2021 | Beeckler et al. |
| 11,051,877 B2 | 7/2021 | Sliwa et al. |
| 11,109,788 B2 | 9/2021 | Rottmann et al. |
| 11,116,435 B2 | 9/2021 | Urman et al. |
| 11,129,574 B2 | 9/2021 | Cohen et al. |
| 11,160,482 B2 | 11/2021 | Solis |
| 11,164,371 B2 | 11/2021 | Yellin et al. |
| 2001/0031961 A1 | 10/2001 | Hooven |
| 2002/0002369 A1 | 1/2002 | Hood |
| 2002/0055674 A1* | 5/2002 | Ben-Haim ............ A61B 5/6858 600/374 |
| 2002/0065455 A1 | 5/2002 | Ben-Haim et al. |
| 2002/0068931 A1 | 6/2002 | Wong et al. |
| 2002/0077627 A1 | 6/2002 | Johnson et al. |
| 2002/0160134 A1 | 10/2002 | Ogushi et al. |
| 2003/0018327 A1 | 1/2003 | Truckai et al. |
| 2003/0028183 A1 | 2/2003 | Sanchez et al. |
| 2003/0050637 A1 | 3/2003 | Maguire et al. |
| 2003/0060820 A1 | 3/2003 | Maguire et al. |
| 2003/0144658 A1 | 7/2003 | Schwartz et al. |
| 2003/0176799 A1* | 9/2003 | Beatty .................. A61B 5/0422 600/509 |
| 2004/0122445 A1 | 6/2004 | Butler et al. |
| 2004/0147920 A1 | 7/2004 | Keidar |
| 2004/0210121 A1 | 10/2004 | Fuimaono et al. |
| 2004/0225285 A1 | 11/2004 | Gibson |
| 2005/0070887 A1 | 3/2005 | Taimisto et al. |
| 2005/0119686 A1 | 6/2005 | Clubb |
| 2006/0009689 A1* | 1/2006 | Fuimaono ............. A61B 5/061 600/374 |
| 2006/0009690 A1 | 1/2006 | Fuimaono et al. |
| 2006/0013595 A1 | 1/2006 | Trezza et al. |
| 2006/0100669 A1 | 5/2006 | Fuimaono et al. |
| 2006/0106375 A1 | 5/2006 | Werneth et al. |
| 2006/0135953 A1 | 6/2006 | Kania et al. |
| 2007/0071792 A1 | 3/2007 | Varner et al. |
| 2007/0080322 A1 | 4/2007 | Walba |
| 2007/0083194 A1 | 4/2007 | Kunis et al. |
| 2007/0093806 A1 | 4/2007 | Desai et al. |
| 2007/0276212 A1 | 11/2007 | Fuimaono et al. |
| 2007/0287994 A1 | 12/2007 | Patel |
| 2008/0018891 A1 | 1/2008 | Hell et al. |
| 2008/0021313 A1 | 1/2008 | Eidenschink et al. |
| 2008/0051707 A1 | 2/2008 | Phan et al. |
| 2008/0140072 A1 | 6/2008 | Stangenes et al. |
| 2008/0183132 A1 | 7/2008 | Davies et al. |
| 2008/0188912 A1 | 8/2008 | Stone et al. |
| 2008/0202637 A1 | 8/2008 | Hector et al. |
| 2008/0208186 A1 | 8/2008 | Slater |
| 2008/0234564 A1 | 9/2008 | Beatty et al. |
| 2008/0249463 A1 | 10/2008 | Pappone et al. |
| 2008/0262489 A1 | 10/2008 | Steinke |
| 2008/0281312 A1 | 11/2008 | Werneth et al. |
| 2009/0163890 A1 | 6/2009 | Clifford et al. |
| 2009/0182318 A1 | 7/2009 | Abboud et al. |
| 2009/0270850 A1 | 10/2009 | Zhou et al. |
| 2010/0069836 A1 | 3/2010 | Satake |
| 2010/0114269 A1 | 5/2010 | Wittenberger et al. |
| 2010/0204560 A1 | 8/2010 | Salahieh et al. |
| 2010/0256629 A1 | 10/2010 | Wylie et al. |
| 2010/0324552 A1 | 12/2010 | Kauphusman et al. |
| 2011/0118632 A1 | 5/2011 | Sinelnikov et al. |
| 2011/0118726 A1 | 5/2011 | De La Rama et al. |
| 2011/0130648 A1 | 6/2011 | Beeckler et al. |
| 2011/0160574 A1 | 6/2011 | Harlev et al. |
| 2011/0190625 A1 | 8/2011 | Harlev et al. |
| 2011/0245756 A1 | 10/2011 | Arora et al. |
| 2011/0282338 A1 | 11/2011 | Fojtik |
| 2011/0295248 A1 | 12/2011 | Wallace et al. |
| 2011/0301587 A1 | 12/2011 | Deem et al. |
| 2011/0301597 A1 | 12/2011 | McDaniel et al. |
| 2011/0313286 A1 | 12/2011 | Whayne et al. |
| 2012/0019107 A1 | 1/2012 | Gabl et al. |
| 2012/0029511 A1 | 2/2012 | Smith et al. |
| 2012/0065503 A1 | 3/2012 | Rogers et al. |
| 2012/0071870 A1 | 3/2012 | Salahieh et al. |
| 2012/0079427 A1 | 3/2012 | Carmichael et al. |
| 2012/0101413 A1 | 4/2012 | Beetel et al. |
| 2012/0101538 A1 | 4/2012 | Ballakur et al. |
| 2012/0143177 A1 | 6/2012 | Avitall |
| 2012/0143293 A1 | 6/2012 | Mauch et al. |
| 2012/0165803 A1* | 6/2012 | Bencini ................ A61B 18/02 606/21 |
| 2012/0191079 A1 | 7/2012 | Moll et al. |
| 2012/0209260 A1 | 8/2012 | Lambert et al. |
| 2013/0085360 A1 | 4/2013 | Grunewald |
| 2013/0090649 A1 | 4/2013 | Smith et al. |
| 2013/0109982 A1 | 5/2013 | Sato et al. |
| 2013/0150693 A1 | 6/2013 | D'Angelo et al. |
| 2013/0165916 A1 | 6/2013 | Mathur et al. |
| 2013/0165941 A1 | 6/2013 | Murphy |
| 2013/0165990 A1 | 6/2013 | Mathur et al. |
| 2013/0169624 A1 | 7/2013 | Bourier et al. |
| 2013/0172872 A1 | 7/2013 | Subramaniam et al. |
| 2013/0172883 A1 | 7/2013 | Lopes et al. |
| 2013/0178850 A1 | 7/2013 | Lopes et al. |
| 2013/0190587 A1 | 7/2013 | Lopes et al. |
| 2013/0261692 A1 | 10/2013 | Cardinal et al. |
| 2013/0274562 A1 | 10/2013 | Ghaffari et al. |
| 2013/0274658 A1 | 10/2013 | Steinke et al. |
| 2013/0282084 A1 | 10/2013 | Mathur et al. |
| 2013/0296852 A1 | 11/2013 | Madjarov et al. |
| 2013/0318439 A1 | 11/2013 | Landis et al. |
| 2014/0012242 A1 | 1/2014 | Lee et al. |
| 2014/0018662 A1* | 1/2014 | Montag ................ A61B 5/062 600/409 |
| 2014/0018788 A1 | 1/2014 | Engelman et al. |
| 2014/0025069 A1 | 1/2014 | Willard et al. |
| 2014/0031813 A1 | 1/2014 | Tellio et al. |
| 2014/0052118 A1 | 2/2014 | Laske et al. |
| 2014/0058197 A1 | 2/2014 | Salahieh et al. |
| 2014/0121470 A1 | 5/2014 | Scharf et al. |
| 2014/0148805 A1 | 5/2014 | Stewart et al. |
| 2014/0180147 A1* | 6/2014 | Thakur ................ A61B 5/042 600/508 |
| 2014/0180151 A1 | 6/2014 | Maskara et al. |
| 2014/0180152 A1 | 6/2014 | Maskara et al. |
| 2014/0227437 A1 | 8/2014 | DeBoer et al. |
| 2014/0243821 A1 | 8/2014 | Salahieh et al. |
| 2014/0257069 A1 | 9/2014 | Eliason et al. |
| 2014/0275993 A1 | 9/2014 | Ballakur |
| 2014/0276712 A1 | 9/2014 | Mallin et al. |
| 2014/0276756 A1 | 9/2014 | Hill |
| 2014/0276811 A1 | 9/2014 | Koblish et al. |

(56) References Cited

U.S. PATENT DOCUMENTS

| | | |
|---|---|---|
| 2014/0288546 A1 | 9/2014 | Sherman et al. |
| 2014/0309512 A1 | 10/2014 | Govari et al. |
| 2014/0330266 A1 | 11/2014 | Thompson et al. |
| 2014/0357956 A1 | 12/2014 | Salahieh et al. |
| 2014/0364926 A1* | 12/2014 | Nguyen .............. A61B 18/1482 607/113 |
| 2015/0005799 A1 | 1/2015 | Lindquist et al. |
| 2015/0011991 A1 | 1/2015 | Buysman et al. |
| 2015/0025532 A1 | 1/2015 | Hanson et al. |
| 2015/0025533 A1 | 1/2015 | Groff et al. |
| 2015/0045863 A1 | 2/2015 | Litscher et al. |
| 2015/0057655 A1 | 2/2015 | Osypka |
| 2015/0067512 A1 | 3/2015 | Roswell |
| 2015/0080693 A1 | 3/2015 | Solis |
| 2015/0080883 A1 | 3/2015 | Haverkost et al. |
| 2015/0105770 A1 | 4/2015 | Amit |
| 2015/0105774 A1 | 4/2015 | Lindquist et al. |
| 2015/0112256 A1 | 4/2015 | Byrne et al. |
| 2015/0112321 A1 | 4/2015 | Cadouri |
| 2015/0119875 A1 | 4/2015 | Fischell et al. |
| 2015/0119878 A1 | 4/2015 | Heisel et al. |
| 2015/0133919 A1 | 5/2015 | McDaniel et al. |
| 2015/0141982 A1 | 5/2015 | Lee |
| 2015/0157382 A1 | 6/2015 | Avitall et al. |
| 2015/0208942 A1 | 7/2015 | Bar-Tal et al. |
| 2015/0216591 A1 | 8/2015 | Cao et al. |
| 2015/0216650 A1 | 8/2015 | Shaltis |
| 2015/0250424 A1 | 9/2015 | Govari et al. |
| 2015/0265329 A1 | 9/2015 | Lalonde et al. |
| 2015/0265339 A1 | 9/2015 | Lindquist et al. |
| 2015/0265812 A1 | 9/2015 | Lalonde |
| 2015/0270634 A1 | 9/2015 | Buesseler et al. |
| 2015/0272667 A1 | 10/2015 | Govari et al. |
| 2015/0327805 A1 | 11/2015 | Ben-Haim |
| 2015/0341752 A1 | 11/2015 | Flynn |
| 2015/0342532 A1 | 12/2015 | Basu et al. |
| 2015/0351652 A1* | 12/2015 | Marecki .............. A61B 5/6856 600/374 |
| 2015/0366508 A1 | 12/2015 | Chou et al. |
| 2016/0000499 A1 | 1/2016 | Lennox et al. |
| 2016/0051321 A1 | 2/2016 | Salahieh et al. |
| 2016/0081746 A1 | 3/2016 | Solis |
| 2016/0085431 A1 | 3/2016 | Kim et al. |
| 2016/0106499 A1 | 4/2016 | Ogata et al. |
| 2016/0113582 A1 | 4/2016 | Altmann et al. |
| 2016/0113709 A1 | 4/2016 | Maor |
| 2016/0166306 A1 | 6/2016 | Pageard |
| 2016/0175041 A1 | 6/2016 | Govari et al. |
| 2016/0183877 A1 | 6/2016 | Williams et al. |
| 2016/0196635 A1 | 7/2016 | Cho et al. |
| 2016/0228023 A1 | 8/2016 | Govari |
| 2016/0228062 A1 | 8/2016 | Altmann et al. |
| 2016/0256305 A1 | 9/2016 | Longo et al. |
| 2016/0278853 A1 | 9/2016 | Ogle et al. |
| 2016/0302858 A1 | 10/2016 | Bencini |
| 2016/0338770 A1 | 11/2016 | Bar-Tal et al. |
| 2016/0374748 A9 | 12/2016 | Salahieh et al. |
| 2017/0027638 A1 | 2/2017 | Solis |
| 2017/0042614 A1 | 2/2017 | Salahieh et al. |
| 2017/0042615 A1 | 2/2017 | Salahieh et al. |
| 2017/0065227 A1 | 3/2017 | Marrs et al. |
| 2017/0071543 A1 | 3/2017 | Basu et al. |
| 2017/0071544 A1 | 3/2017 | Basu et al. |
| 2017/0071665 A1 | 3/2017 | Solis |
| 2017/0080192 A1 | 3/2017 | Giasolli et al. |
| 2017/0095173 A1 | 4/2017 | Bar-Tal et al. |
| 2017/0100187 A1 | 4/2017 | Basu et al. |
| 2017/0143227 A1 | 5/2017 | Marecki et al. |
| 2017/0143359 A1 | 5/2017 | Nguyen et al. |
| 2017/0156790 A1 | 6/2017 | Aujla |
| 2017/0164464 A1 | 6/2017 | Weinkam et al. |
| 2017/0172442 A1 | 6/2017 | Govari |
| 2017/0185702 A1 | 6/2017 | Auerbach et al. |
| 2017/0202515 A1 | 7/2017 | Zrihem et al. |
| 2017/0221262 A1 | 8/2017 | Laughner et al. |
| 2017/0224958 A1 | 8/2017 | Cummings et al. |
| 2017/0265812 A1 | 9/2017 | Williams et al. |
| 2017/0281031 A1 | 10/2017 | Houben et al. |
| 2017/0281268 A1 | 10/2017 | Tran et al. |
| 2017/0296125 A1 | 10/2017 | Altmann et al. |
| 2017/0296251 A1 | 10/2017 | Wu et al. |
| 2017/0311829 A1 | 11/2017 | Beeckler et al. |
| 2017/0311893 A1 | 11/2017 | Beeckler et al. |
| 2017/0312022 A1 | 11/2017 | Beeckler et al. |
| 2017/0347896 A1 | 12/2017 | Keyes et al. |
| 2017/0347959 A1 | 12/2017 | Guta et al. |
| 2017/0354338 A1 | 12/2017 | Levin et al. |
| 2017/0354339 A1 | 12/2017 | Zeidan et al. |
| 2017/0354364 A1 | 12/2017 | Bar-Tal et al. |
| 2018/0008203 A1 | 1/2018 | Iyun et al. |
| 2018/0028084 A1 | 2/2018 | Williams et al. |
| 2018/0049803 A1 | 2/2018 | Solis |
| 2018/0074693 A1 | 3/2018 | Jones et al. |
| 2018/0085064 A1 | 3/2018 | Auerbach et al. |
| 2018/0110562 A1 | 4/2018 | Govari et al. |
| 2018/0125575 A1 | 5/2018 | Schwartz et al. |
| 2018/0132749 A1 | 5/2018 | Govari et al. |
| 2018/0137687 A1 | 5/2018 | Katz et al. |
| 2018/0160936 A1 | 6/2018 | Govari et al. |
| 2018/0160978 A1 | 6/2018 | Cohen et al. |
| 2018/0168511 A1 | 6/2018 | Hall et al. |
| 2018/0184982 A1 | 7/2018 | Basu et al. |
| 2018/0192958 A1 | 7/2018 | Wu |
| 2018/0206792 A1 | 7/2018 | Auerbach et al. |
| 2018/0235692 A1 | 8/2018 | Efimov et al. |
| 2018/0249959 A1 | 9/2018 | Osypka |
| 2018/0256109 A1 | 9/2018 | Wu et al. |
| 2018/0256247 A1 | 9/2018 | Govari et al. |
| 2018/0279954 A1 | 10/2018 | Hayam et al. |
| 2018/0280080 A1 | 10/2018 | Govari et al. |
| 2018/0303414 A1 | 10/2018 | Toth et al. |
| 2018/0310987 A1 | 11/2018 | Altmann et al. |
| 2018/0311497 A1 | 11/2018 | Viswanathan et al. |
| 2018/0333162 A1 | 11/2018 | Saab |
| 2018/0338722 A1 | 11/2018 | Altmann et al. |
| 2018/0344188 A1 | 12/2018 | Govari |
| 2018/0344202 A1 | 12/2018 | Bar-Tal et al. |
| 2018/0344251 A1 | 12/2018 | Harlev et al. |
| 2018/0344393 A1 | 12/2018 | Gruba et al. |
| 2018/0360534 A1 | 12/2018 | Teplitsky et al. |
| 2018/0365355 A1 | 12/2018 | Auerbach et al. |
| 2018/0368927 A1 | 12/2018 | Lyons et al. |
| 2019/0000540 A1 | 1/2019 | Cohen et al. |
| 2019/0008582 A1 | 1/2019 | Govari et al. |
| 2019/0015007 A1 | 1/2019 | Rottmann et al. |
| 2019/0030328 A1 | 1/2019 | Stewart et al. |
| 2019/0053708 A1 | 2/2019 | Gliner |
| 2019/0059766 A1 | 2/2019 | Houben et al. |
| 2019/0059818 A1 | 2/2019 | Herrera et al. |
| 2019/0060622 A1 | 2/2019 | Beeckler |
| 2019/0069950 A1 | 3/2019 | Viswanathan et al. |
| 2019/0069954 A1 | 3/2019 | Cohen et al. |
| 2019/0117111 A1 | 4/2019 | Osadchy et al. |
| 2019/0117303 A1 | 4/2019 | Claude et al. |
| 2019/0117315 A1 | 4/2019 | Keyes et al. |
| 2019/0125439 A1 | 5/2019 | Rohl et al. |
| 2019/0133552 A1 | 5/2019 | Shemesh et al. |
| 2019/0142293 A1 | 5/2019 | Solis |
| 2019/0143079 A1 | 5/2019 | Beeckler et al. |
| 2019/0164633 A1 | 5/2019 | Ingel et al. |
| 2019/0167137 A1 | 6/2019 | Bar-Tal et al. |
| 2019/0167140 A1 | 6/2019 | Williams et al. |
| 2019/0175262 A1 | 6/2019 | Govari et al. |
| 2019/0175263 A1 | 6/2019 | Altmann et al. |
| 2019/0183567 A1 | 6/2019 | Govari et al. |
| 2019/0188909 A1 | 6/2019 | Yellin et al. |
| 2019/0201664 A1 | 7/2019 | Govari |
| 2019/0201669 A1 | 7/2019 | Govari et al. |
| 2019/0209089 A1 | 7/2019 | Baram et al. |
| 2019/0216346 A1 | 7/2019 | Ghodrati et al. |
| 2019/0216347 A1 | 7/2019 | Ghodrati et al. |
| 2019/0217065 A1 | 7/2019 | Govari et al. |
| 2019/0231421 A1 | 8/2019 | Viswanathan et al. |
| 2019/0231423 A1 | 8/2019 | Weinkam et al. |

(56) References Cited

U.S. PATENT DOCUMENTS

| | | |
|---|---|---|
| 2019/0239811 A1 | 8/2019 | Just et al. |
| 2019/0246935 A1 | 8/2019 | Govari et al. |
| 2019/0297441 A1 | 9/2019 | Dehe et al. |
| 2019/0298441 A1 | 10/2019 | Clark et al. |
| 2019/0298442 A1 | 10/2019 | Ogata et al. |
| 2019/0314083 A1 | 10/2019 | Herrera et al. |
| 2019/0328260 A1 | 10/2019 | Zeidan et al. |
| 2019/0343580 A1 | 11/2019 | Nguyen et al. |
| 2019/0365451 A1 | 12/2019 | Jung, Jr. |
| 2020/0000518 A1 | 1/2020 | Kiernan et al. |
| 2020/0001054 A1 | 1/2020 | Jimenez et al. |
| 2020/0008705 A1 | 1/2020 | Ziv-Ari et al. |
| 2020/0008869 A1 | 1/2020 | Byrd |
| 2020/0009378 A1 | 1/2020 | Stewart et al. |
| 2020/0015693 A1 | 1/2020 | Beeckler et al. |
| 2020/0015890 A1 | 1/2020 | To et al. |
| 2020/0022653 A1 | 1/2020 | Moisa |
| 2020/0029845 A1 | 1/2020 | Baram et al. |
| 2020/0046421 A1 | 2/2020 | Govari |
| 2020/0046423 A1 | 2/2020 | Viswanathan et al. |
| 2020/0060569 A1 | 2/2020 | Tegg |
| 2020/0077959 A1 | 3/2020 | Altmann et al. |
| 2020/0085497 A1 | 3/2020 | Zhang et al. |
| 2020/0093539 A1 | 3/2020 | Long et al. |
| 2020/0129089 A1 | 4/2020 | Gliner et al. |
| 2020/0129125 A1 | 4/2020 | Govari et al. |
| 2020/0129128 A1 | 4/2020 | Gliner et al. |
| 2020/0155226 A1 | 5/2020 | Valls et al. |
| 2020/0179650 A1 | 6/2020 | Beeckler et al. |
| 2020/0196896 A1 | 6/2020 | Solis |
| 2020/0205689 A1 | 7/2020 | Squires et al. |
| 2020/0205690 A1 | 7/2020 | Williams et al. |
| 2020/0205737 A1 | 7/2020 | Beeckler |
| 2020/0205876 A1 | 7/2020 | Govari |
| 2020/0205892 A1 | 7/2020 | Viswanathan et al. |
| 2020/0206461 A1 | 7/2020 | Govari et al. |
| 2020/0206498 A1 | 7/2020 | Arora et al. |
| 2020/0289197 A1 | 9/2020 | Viswanathan et al. |
| 2020/0297234 A1 | 9/2020 | Houben et al. |
| 2020/0297281 A1 | 9/2020 | Basu et al. |
| 2020/0305726 A1 | 10/2020 | Salvestro et al. |
| 2020/0305946 A1 | 10/2020 | DeSimone et al. |
| 2020/0397328 A1 | 12/2020 | Altmann et al. |
| 2020/0398048 A1 | 12/2020 | Krimsky et al. |
| 2021/0015549 A1 | 1/2021 | Haghighi-Mood et al. |
| 2021/0022684 A1 | 1/2021 | Govari et al. |
| 2021/0045805 A1 | 2/2021 | Govari et al. |
| 2021/0059549 A1 | 3/2021 | Urman et al. |
| 2021/0059550 A1 | 3/2021 | Urman et al. |
| 2021/0059608 A1 | 3/2021 | Beeckler et al. |
| 2021/0059743 A1 | 3/2021 | Govari |
| 2021/0059747 A1 | 3/2021 | Krans et al. |
| 2021/0077184 A1 | 3/2021 | Basu et al. |
| 2021/0082157 A1 | 3/2021 | Rosenberg et al. |
| 2021/0085200 A1 | 3/2021 | Auerbach et al. |
| 2021/0085204 A1 | 3/2021 | Auerbach et al. |
| 2021/0085215 A1 | 3/2021 | Auerbach et al. |
| 2021/0085387 A1 | 3/2021 | Amit et al. |
| 2021/0093292 A1 | 4/2021 | Baram et al. |
| 2021/0093294 A1 | 4/2021 | Shemesh et al. |
| 2021/0093374 A1 | 4/2021 | Govari et al. |
| 2021/0093377 A1 | 4/2021 | Herrera et al. |
| 2021/0100612 A1 | 4/2021 | Baron et al. |
| 2021/0113822 A1 | 4/2021 | Beeckler et al. |
| 2021/0127999 A1 | 5/2021 | Govari et al. |
| 2021/0128010 A1 | 5/2021 | Govari et al. |
| 2021/0133516 A1 | 5/2021 | Govari et al. |
| 2021/0145282 A1 | 5/2021 | Bar-Tal et al. |
| 2021/0169421 A1 | 6/2021 | Govari |
| 2021/0169567 A1 | 6/2021 | Govari et al. |
| 2021/0169568 A1 | 6/2021 | Govari et al. |
| 2021/0177294 A1 | 6/2021 | Gliner et al. |
| 2021/0177356 A1 | 6/2021 | Gliner et al. |
| 2021/0178166 A1 | 6/2021 | Govari et al. |
| 2021/0186363 A1 | 6/2021 | Gliner et al. |
| 2021/0187241 A1 | 6/2021 | Govari et al. |
| 2021/0196372 A1 | 7/2021 | Altmann et al. |
| 2021/0196394 A1 | 7/2021 | Govari et al. |
| 2021/0212591 A1 | 7/2021 | Govari et al. |
| 2021/0219904 A1 | 7/2021 | Yarnitsky et al. |
| 2021/0278936 A1 | 9/2021 | Katz et al. |
| 2021/0282659 A1 | 9/2021 | Govari et al. |
| 2021/0307815 A1 | 10/2021 | Govari et al. |
| 2021/0308424 A1 | 10/2021 | Beeckler et al. |
| 2021/0338319 A1 | 11/2021 | Govari et al. |

FOREIGN PATENT DOCUMENTS

| | | |
|---|---|---|
| CN | 102458566 A | 5/2012 |
| CN | 203539434 U | 4/2014 |
| CN | 104244856 A | 12/2014 |
| CN | 104546117 A | 4/2015 |
| CN | 105105844 A | 12/2015 |
| CN | 105473091 A | 4/2016 |
| CN | 105473093 A | 4/2016 |
| CN | 111248993 A | 6/2020 |
| CN | 111248996 A | 6/2020 |
| EP | 0668740 A1 | 8/1995 |
| EP | 0779059 A1 | 6/1997 |
| EP | 0644738 B1 | 3/2000 |
| EP | 0727183 B1 | 11/2002 |
| EP | 0727184 B1 | 12/2002 |
| EP | 1790304 A2 | 5/2007 |
| EP | 2749214 A1 | 7/2014 |
| EP | 2783651 A1 | 10/2014 |
| EP | 2865350 A2 | 4/2015 |
| EP | 2875790 A2 | 5/2015 |
| EP | 2 915 498 A1 | 9/2015 |
| EP | 2699151 B1 | 11/2015 |
| EP | 2699152 B1 | 11/2015 |
| EP | 2699153 B1 | 12/2015 |
| EP | 2498706 B1 | 4/2016 |
| EP | 3 184 037 A1 | 6/2017 |
| EP | 2578173 B1 | 6/2017 |
| EP | 3238645 A1 | 11/2017 |
| EP | 3238646 A2 | 11/2017 |
| EP | 3238648 A1 | 11/2017 |
| EP | 3251622 A1 | 12/2017 |
| EP | 2884931 B1 | 1/2018 |
| EP | 3300680 A1 | 4/2018 |
| EP | 3315087 A1 | 5/2018 |
| EP | 3332727 A2 | 6/2018 |
| EP | 2349440 B1 | 8/2019 |
| EP | 3571983 A2 | 11/2019 |
| EP | 3318211 B1 | 12/2019 |
| EP | 3581135 A1 | 12/2019 |
| EP | 3586778 A1 | 1/2020 |
| EP | 2736434 B1 | 2/2020 |
| EP | 3451962 B1 | 3/2020 |
| EP | 3653153 A1 | 5/2020 |
| EP | 3972510 A1 | 3/2022 |
| JP | H06261951 A | 9/1994 |
| JP | H1176233 A | 3/1999 |
| JP | 2000504242 A | 4/2000 |
| JP | 2005052424 A | 3/2005 |
| JP | 2005161077 A | 6/2005 |
| JP | 2010507404 A | 3/2010 |
| JP | 2012024156 A | 2/2012 |
| JP | 2013013726 A | 1/2013 |
| JP | 2013078587 A | 5/2013 |
| JP | 2013529109 A | 7/2013 |
| JP | 2014073384 A | 4/2014 |
| JP | 2014529419 A | 11/2014 |
| JP | 2015503365 A | 2/2015 |
| JP | 2015100706 A | 6/2015 |
| JP | 2015112113 A | 6/2015 |
| JP | 2015112114 A | 6/2015 |
| JP | 2015518776 A | 7/2015 |
| JP | 2016515442 A | 5/2016 |
| JP | 2016116863 A | 6/2016 |
| WO | 9421167 A1 | 9/1994 |
| WO | 9421169 A1 | 9/1994 |
| WO | 9625095 A1 | 8/1996 |
| WO | 9634560 A1 | 11/1996 |

(56) References Cited

FOREIGN PATENT DOCUMENTS

| | | | |
|---|---|---|---|
| WO | WO-9724983 A2 * | 7/1997 | ............ A61B 34/20 |
| WO | 0056237 A2 | 9/2000 | |
| WO | 0182814 B1 | 5/2002 | |
| WO | 02102231 A2 | 12/2002 | |
| WO | 2004087249 A2 | 10/2004 | |
| WO | 2005041748 A2 | 5/2005 | |
| WO | 2008049087 A2 | 4/2008 | |
| WO | 2011143468 A2 | 11/2011 | |
| WO | 2012100185 A2 | 7/2012 | |
| WO | 2013049601 A2 | 4/2013 | |
| WO | 2013052852 A1 | 4/2013 | |
| WO | 2013052919 A2 | 4/2013 | |
| WO | 2013154776 A2 | 10/2013 | |
| WO | 2013162884 A1 | 10/2013 | |
| WO | 2013173917 A1 | 11/2013 | |
| WO | 2013176881 A1 | 11/2013 | |
| WO | 2014168987 A1 | 10/2014 | |
| WO | 2014176205 A1 | 10/2014 | |
| WO | 2015049784 A1 | 4/2015 | |
| WO | 2016019760 A1 | 2/2016 | |
| WO | 2016044687 A1 | 3/2016 | |
| WO | WO 2016/044687 A1 | 3/2016 | |
| WO | 2016183337 A2 | 11/2016 | |
| WO | 2016210437 A1 | 12/2016 | |
| WO | 2017024306 A1 | 2/2017 | |
| WO | 2017087549 A1 | 5/2017 | |
| WO | 2018106569 A1 | 6/2018 | |
| WO | 2018111600 A1 | 6/2018 | |
| WO | 2018129133 A1 | 7/2018 | |
| WO | 2018191149 A1 | 10/2018 | |
| WO | 2019084442 A1 | 5/2019 | |
| WO | 2019095020 A1 | 5/2019 | |
| WO | 2019143960 A1 | 7/2019 | |
| WO | 2020026217 A1 | 2/2020 | |
| WO | 2020206328 A1 | 10/2020 | |

OTHER PUBLICATIONS

European Search Report dated Jul. 13, 2021, EP Application No. EP 21 18 0538.
Notification of Reasons for Refusal (English translation) dated Mar. 1, 2022, from corresponding Japanese Application No. 2019-566155.
First Office Action (English translation) dated Sep. 21, 2022, from corresponding Chinese Application No. 201880036063.9.
Second Office Action (English translation) dated Feb. 19, 2023, from corresponding Chinese Application No. 201880036063.9.
Examination Report dated May 2, 2023, from corresponding European Application No. 21180538.7.
Extended European Search Report dated Jul. 22, 2021, from corresponding European Application No. 21180538.7.
Angela O., "AF Symposium 2017: First-in-Man Study Shows Promising Results with a Multi-Electrode Radiofrequency Balloon for Paroxysmal AF Treatment," Cardiac Rhythm News, Jan. 20, 2017, 2 Pages, [Retrieved on Dec. 16, 2020] Retrieved from URL: https://cardiacrhythmnews.com/fist-in-man-study-shows-promising-results-with-a-multi-electrode-radiofrequency-balloon-for-paroxysmal-af-treatment/.
Casella M., et al., "Ablation Index as a Predictor of Long-Term Efficacy in Premature Ventricular Complex Ablation: A Regional Target Value Analysis," Heart Rhythm Society, Jun. 2019, vol. 16, No. 6, pp. 888-895.
Co-Pending U.S. Appl. No. 14/578,807, filed Dec. 22, 2014, 21 pages.
Das M., et al., "Ablation Index, a Novel Marker of Ablation Lesion Quality: Prediction of Pulmonary Vein Reconnection at Repeat Electrophysiology Study and Regional Differences in Target Values," Europace, 2017, Published Online May 31, 2016, vol. 19, pp. 775-783.
Dorobantu M., et al., "Oral Anticoagulation During Atrial Fibrillation Ablation: Facts and Controversies," Cor et Vasa, 2013, Accepted on Dec. 3, 2012, vol. 55, No. 2, pp. e101-e106, Retrieved from URL: https://www.sciencedirect.com/science/article/pii/S0010865012001415.
Extended European Search Report for Application No. EP17168513.4 mailed Sep. 18, 2017, 11 pages.
Extended European Search Report for European Application No. 15201723.2, mailed May 11, 2016, 07 Pages.
Extended European Search Report for European Application No. 17168393.1 mailed Dec. 15, 2017, 12 Pages.
Extended European Search Report for European Application No. 17168518.3, mailed Sep. 20, 2017, 9 Pages.
Extended European Search Report for European Application No. 17173893.3, mailed Nov. 6, 2017, 8 Pages.
Extended European Search Report for European Application No. 17201434.2, mailed Feb. 1, 2018, 10 Pages.
Extended European Search Report for European Application No. 17205876.0, mailed Jun. 1, 2018, 13 Pages.
Extended European Search Report for European Application No. 19177365.4, mailed Nov. 8, 2019, 07 Pages.
Extended European Search Report for European Application No. 19183327.6, mailed Nov. 21, 2019, 8 Pages.
Extended European Search Report for European Application No. 20153872.5, mailed May 7, 2020, 9 Pages.
Extended European Search Report for European Application No. 20195648.9, mailed Feb. 12, 2021, 8 Pages.
Fornell D., "Multi-Electrode RF Balloon Efficient for Acute Pulmonary Vein Isolation," Diagnostic and Interventional Cardiology, May 17, 2017, 3 Pages, [Retrieved on Dec. 16, 2020] Retrieved from URL: www.dicardiology.com/article/multi-electrode-rf-balloon-efficient-acute-pulmonary-vein-isolation.
Haines D.E., et al., "The Promise of Pulsed Field Ablation," Dec. 2019, vol. 19, No. 12, 10 pages.
Honarbakhsh S., et al., "Radiofrequency Balloon Catheter Ablation for Paroxysmal Atrial Fibrillation, RADIANCE STUDY—a UK experience," EP Europace, Oct. 2017, vol. 19, No. 1, p. i21, 3 Pages.
International Search Report and Written Opinion for International Application No. PCT/IB2019/052313, mailed Jul. 22, 2019, 8 Pages.
International Search Report and Written Opinion for International Application No. PCT/IB2019/056381, mailed Dec. 17, 2019, 10 pages.
International Search Report and Written Opinion for International Application No. PCT/IB2019/057743, mailed Dec. 6, 2019, 16 Pages.
International Search Report and Written Opinion issued in corresponding International Application No. PCT/IB2019/057742, dated Nov. 28, 2019, 18 Pages.
Nagashima K., et al., "Hot Balloon Versus Cryoballoon Ablation for Atrial Fibrillation," Circulation: Arrhythmia and Electrophysiology, May 2018, vol. 11, No. 5, e005861, 9 Pages.
Napoli N., et al., "For Atrial Fibrillation Ablation, Newer Anticoagulant Reduces Major Bleeds," American College of Cardiology, Mar. 19, 2017, 4 Pages, [Retrieved on Jan. 21, 2022] Retrieved from URL: https://www.acc.org/about-acc/press-releases/2017/03/18/08/47/sun-1045am-for-atrial-fibrillation-ablation-newer-anticoagulant-reduces-major-bleeds.
Okano T., et al., "Wire Perforation Causing Cardiopulmonary Arrest During Radiofrequency Hot Balloon Ablation for Pulmonary Vein Isolation," Journal of Cardiology Cases, Feb. 15, 2019, vol. 19, No. 5, pp. 169-172.
Partial European Search Report for European Application No. 17168393.1 mailed Sep. 13, 2017, 13 Pages.
Partial European Search Report for European Application No. 17205876.0, mailed Feb. 22, 2018, 10 Pages.
Reddy V.Y., et al., "Balloon Catheter Ablation to Treat Paroxysmal Atrial Fibrillation: What is the Level of Pulmonary Venous Isolation?," Heart Rhythm, Mar. 2008, vol. 5, No. 3, pp. 353-360, 3 Pages.
Winkle R.A., et al., "Atrial Fibrillation Ablation Using Open-Irrigated Tip Radiofrequency: Experience with Intraprocedural Activated Clotting Times ≤ 210 Seconds," Heart Rhythm, Jun. 2014, Epub Mar. 27, 2014, vol. 11, No. 6, pp. 963-968.

(56) References Cited

OTHER PUBLICATIONS

Youtube:, "Intensity™ CX4 Professional E-Stim/ Ultrasound Combo," Dec. 22, 2015, 1 Page, [Retrieved on Nov. 19, 2020], Retrieved from URL: https://www.youtube.com/watch?v=76s1QkMWJME].
Youtube: "New Interface TactiCath Contact Force Ablation Catheter," Nov. 26, 2013, 1 Pages, [Retrieved on Nov. 19, 2020], Retrieved from URL: https://www.youtube.com/watch?v=aYvYO8Hpylg].

* cited by examiner

CATHETER SPLINES AS LOCATION SENSORS

CROSS-REFERENCE TO RELATED APPLICATION

This application claims the benefit of U.S. Provisional Patent Application 62/512,263, filed 30 May 2017, which is incorporated herein by reference.

FIELD OF THE INVENTION

The present invention relates generally to catheter navigation, and particularly to methods and systems for locating the position and orientation of a catheter.

BACKGROUND OF THE INVENTION

There is a growing competitive drive in the electrophysiology market to develop basket or balloon type, multi-electrode catheters to provide more detailed electrograms, which result in more accurate maps. The usefulness of the information from such a catheter is greatly improved if location information is also available.

U.S. Pat. No. 6,748,255 to Fuimaono, et al., describes a basket catheter that is stated to be useful for mapping the heart. The catheter comprises an elongated catheter body having proximal and distal ends and at least one lumen therethrough, and a basket-shaped electrode assembly is mounted at the distal end of the catheter body.

U.S. Pat. No. 7,155,270 to Solis, et al., describes a catheter that is stated to be useful for simultaneously mapping multiple points within the heart. The catheter includes a mapping assembly including a plurality of flexible spines, each having a free distal end, and the spines are supported by a support structure that permits the spines to be arranged relative to one another.

U.S. Pat. No. 6,529,756 to Phan, et al., describes a probe that may be used to create circumferential lesions in body tissue and that may also be used to perform mapping functions. The probe includes a collapsible/expandable structure that supports electrodes or other operative elements against the body tissue.

U.S. Pat. No. 6,893,439 to Fleischman, and U.S. Pat. No. 6,939,349 to Fleischman, et al., describe an electrode support structure comprising a guide body having at its distal end a flexible spline leg. The spline leg is flexed to define an arcuate shape to facilitate intimate contact against tissue, and an electrode element is carried by the spline leg for movement along its axis.

U.S. Pat. No. 8,346,339 to Kordis, et al., describes a basket style cardiac mapping catheter having a flexible electrode assembly for detection of cardiac rhythm disorders. The catheter includes a plurality of flexible splines having proximal portions, distal portions and medial portions therein between, and there is an anchor for securably affixing the proximal portions of the splines.

U.S. Pat. No. 8,560,086 to Just, et al., describes a family of catheter electrode assemblies that includes a flexible circuit having a plurality of electrical traces and a substrate, a ring electrode surrounding the flexible circuit and electrically coupled with at least one of the plurality of electrical traces, and an outer covering extending over at least a portion of the electrode.

U.S. Pat. No. 8,644,902 to Kordis, et al., describes a method for detection of cardiac rhythm disorders using a basket style cardiac mapping catheter. The method includes providing a basket assembly including a plurality of flexible splines for guiding a plurality of exposed electrodes, and the electrodes are substantially flat electrodes that are substantially unidirectionally oriented towards a direction outside of the basket.

U.S. Patent Application 2015/0208942 to Bar-Tal, et al., describes how catheterization of the heart may be carried out by inserting a probe having electrodes into a heart of a living subject. The probe may be a basket catheter having multiple ribs, each rib having multiple electrodes.

U.S. Patent Application 2015/0366508 to Chou, et al., describes an expandable catheter assembly with flexible printed circuit board electrical pathways. The expandable assembly can comprise a plurality of splines forming a basket array or basket catheter.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

SUMMARY OF THE DISCLOSURE

An embodiment of the present invention provides an apparatus, including:

a probe having a proximal end and a distal end, the probe being configured to be inserted into an organ of a human patient and defining a probe axis;

at least two conductors positioned on the probe at the distal end;

at least two flexible conductive splines, each conductive spline having a first termination and a second termination, the first terminations being electrically connected together at a region on the probe axis beyond the distal end, each second termination being electrically connected to a respective one of the conductors, the splines being configured to bend into respective arcuate forms that encompass a volume; and a processor configured to receive voltages induced on the splines via the conductors and to calculate a position and orientation of the volume in response to the received voltages.

In a disclosed embodiment the splines are attached to flexible material forming a balloon catheter.

Alternatively, the probe and the splines form a basket catheter.

In a further disclosed embodiment the processor is configured to calculate an ellipticity of the volume in response to the received voltages.

In a yet further disclosed embodiment the apparatus includes at least one magnetic field radiator which generates an alternating magnetic field traversing the volume encompassed by the splines so as to generate the received voltages.

In an alternative embodiment the at least two flexible conductive splines include an even number of splines, and the processor is configured to calculate respective centers and orientations of opposing pairs of splines, and to derive the position and orientation of the volume from the respective centers and orientations.

In a further alternative embodiment the at least two conductors and the at least two flexible conductive splines are distributed symmetrically about the probe axis.

In a yet further alternative embodiment the at least two conductors and the at least two flexible splines are equal in number.

The at least two flexible conductive splines may consist of n splines, where n is an integer greater than or equal to three, and processor is configured to receive a subset of $$\binom{n}{2}$$

voltages induced in respective $$\binom{n}{2}$$

different pairs of splines, and to calculate the position and orientation of the volume in response to the received subset.

Alternatively, the at least two flexible conductive splines may consist of n splines, where n is an integer greater than or equal to two, and the processor is configured to receive $$\binom{n}{2}$$

voltages induced in respective $$\binom{n}{2}$$

different pairs of splines, and to calculate the position and orientation of the volume in response to the received $$\binom{n}{2}$$

voltages.

The processor may be configured to calculate a magnitude of the volume in response to the received voltages. The splines may be attached to flexible material forming a balloon catheter, and the apparatus may further comprise a screen, and the processor may be configured to present on the screen a virtual representation of the balloon catheter in response to the position, the orientation, and the magnitude of the volume.

There is further provided, according to an embodiment of the present invention, a method, including:

configuring a probe, having a proximal end and a distal end, to be inserted into an organ of a human patient, the probe defining a probe axis;

positioning at least two conductors on the probe at the distal end thereof;

providing at least two flexible conductive splines, each conductive spline having a first termination and a second termination;

electrically connecting the first terminations at a region on the probe axis beyond the distal end;

electrically connecting each second termination to a respective one of the conductors;

bending the splines into respective arcuate forms that encompass a volume; and receiving voltages induced on the splines via the conductors and calculating a position and orientation of the volume in response to the received voltages.

The present invention will be more fully understood from the following detailed description of the embodiments thereof, taken together with the drawings in which:

DETAILED DESCRIPTION OF EMBODIMENTS

Overview

It is important, for a basket or balloon catheter probe, that the location of the catheter is known as accurately as possible. Typically, this knowledge is acquired from one or more sensors that are incorporated into the catheter. In contrast, embodiments of the present invention use the splines of the basket or balloon catheter as individual single turn single axis magnetic sensors, the signals from which, when in an alternating magnetic field, providing a location for the sensors. A large area single turn sensor is as accurate as a multi-turn small area sensor because the overall areas of the two types of sensors are similar. The signals from the splines may be used on their own, or together with other location sensors incorporated in the catheter, to provide the location of a volume encompassed by the splines of the catheter.

Thus, an embodiment of the present invention comprises a probe that can be inserted into an organ, typically the heart, of a human patient. The probe, typically cylindrical, defines an axis of symmetry. At least two conductors are positioned on the probe at a distal end thereof, and the probe comprises at least two flexible conductive splines. Each conductive spline has a first termination and a second termination, and the first terminations are electrically connected together at a region on the probe axis beyond the probe distal end. Each second termination is electrically connected to a respective one of the conductors, and the splines are configured to bend in respective arcuate forms that encompass a volume.

A processor receives voltages induced on the splines via the conductors, the voltages being induced on the splines by an alternating magnetic field traversing the volume encompassed by the splines. The processor calculates a position and an orientation of the volume in response to the received voltages.

DETAILED DESCRIPTION

Figure 1:
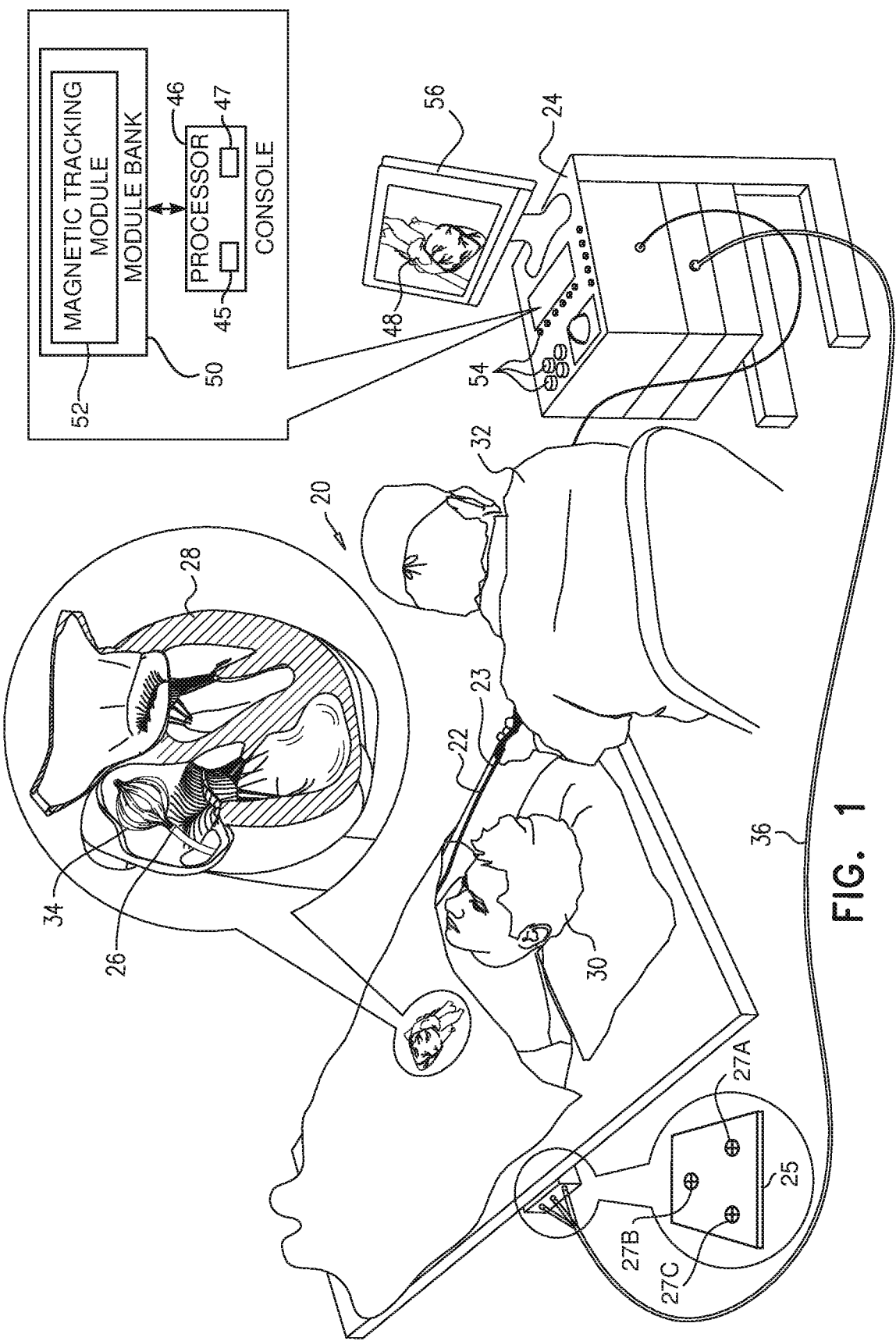
FIG. 1 is a schematic illustration of a medical system comprising a medical probe, according to an embodiment of the present invention.
Figure 2A:
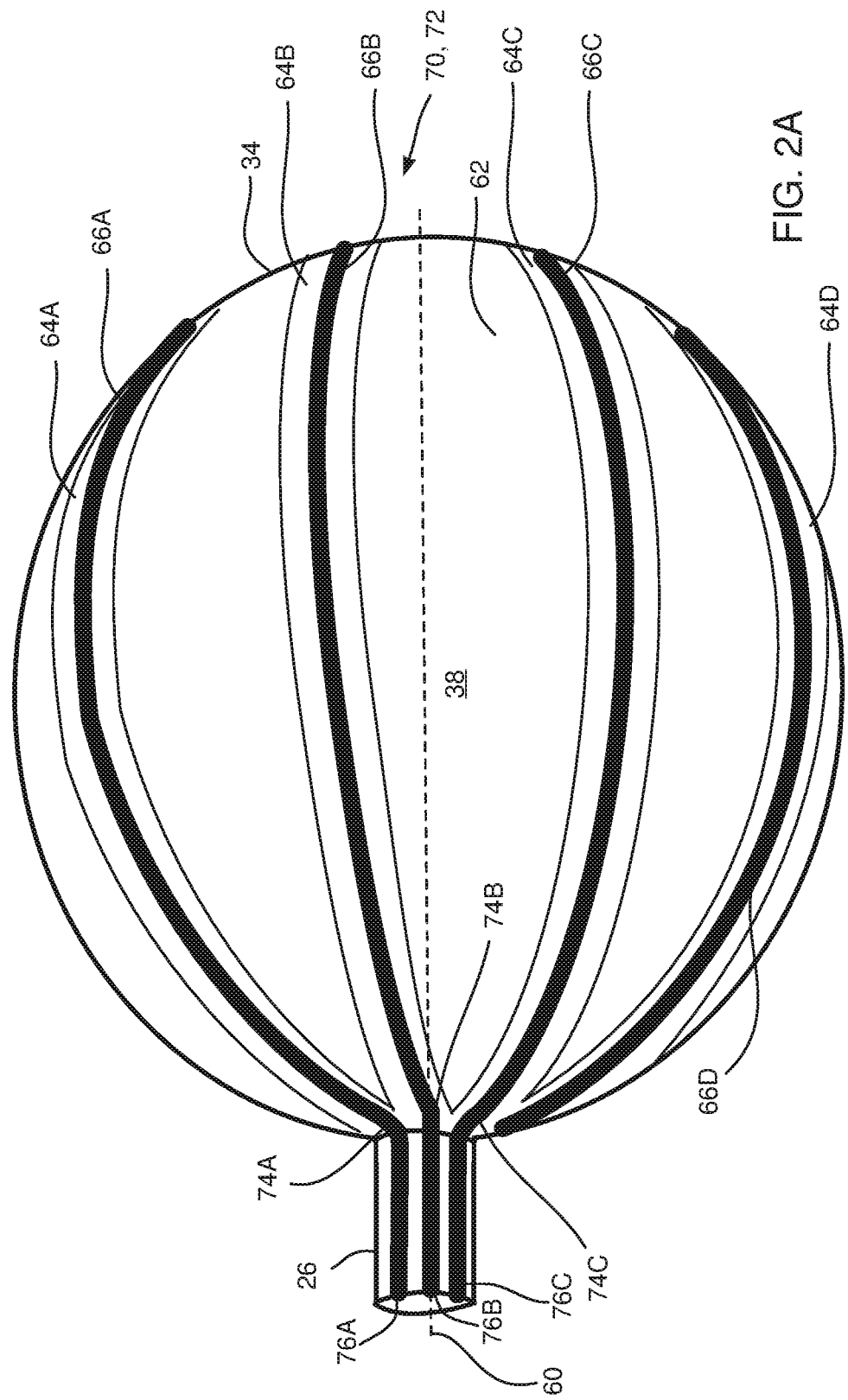
FIGS. 2A, 2B, and 2C are schematic illustrations of a distal end of the probe, according to an embodiment of the present invention.
Figure 2B:
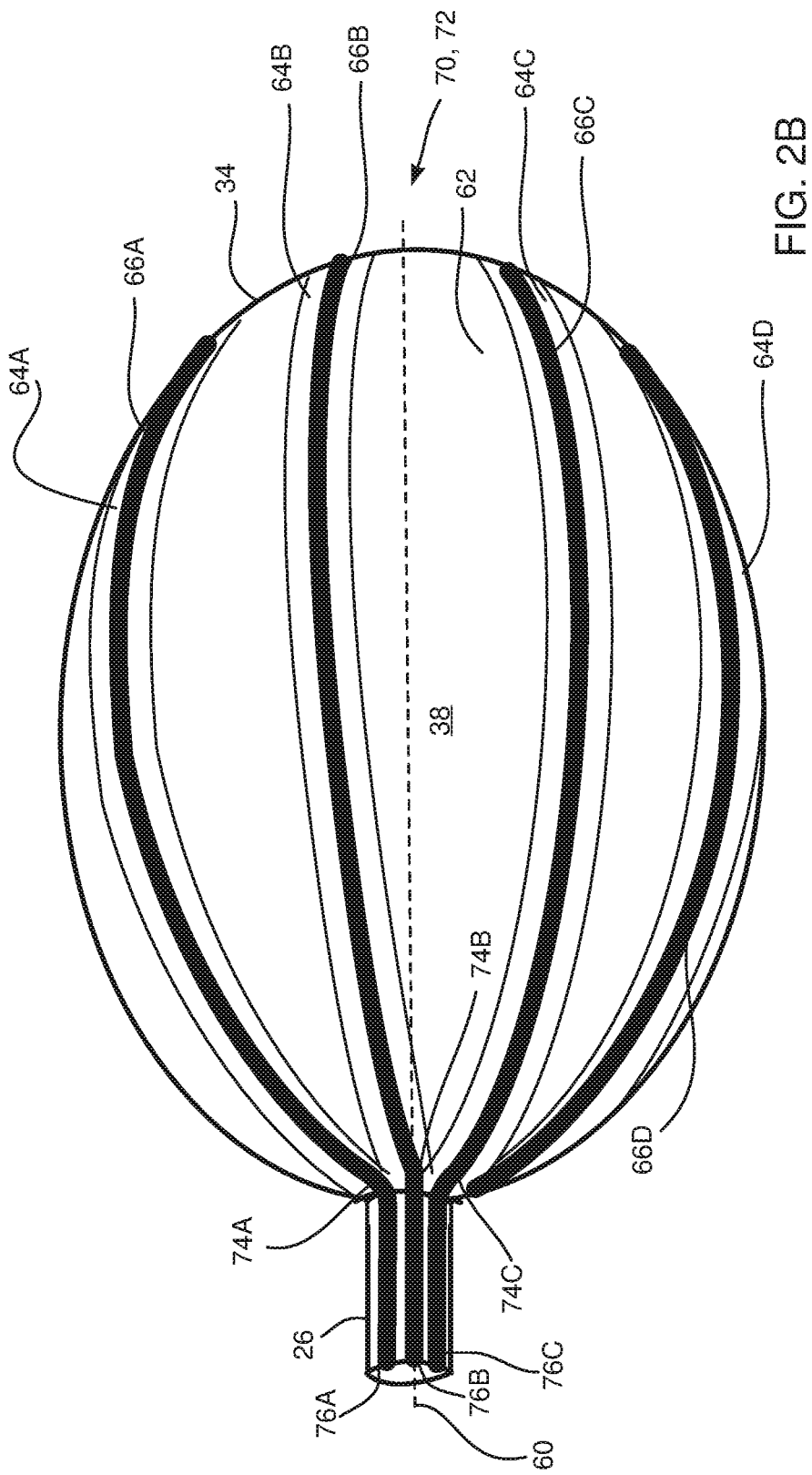
Figure 2C:
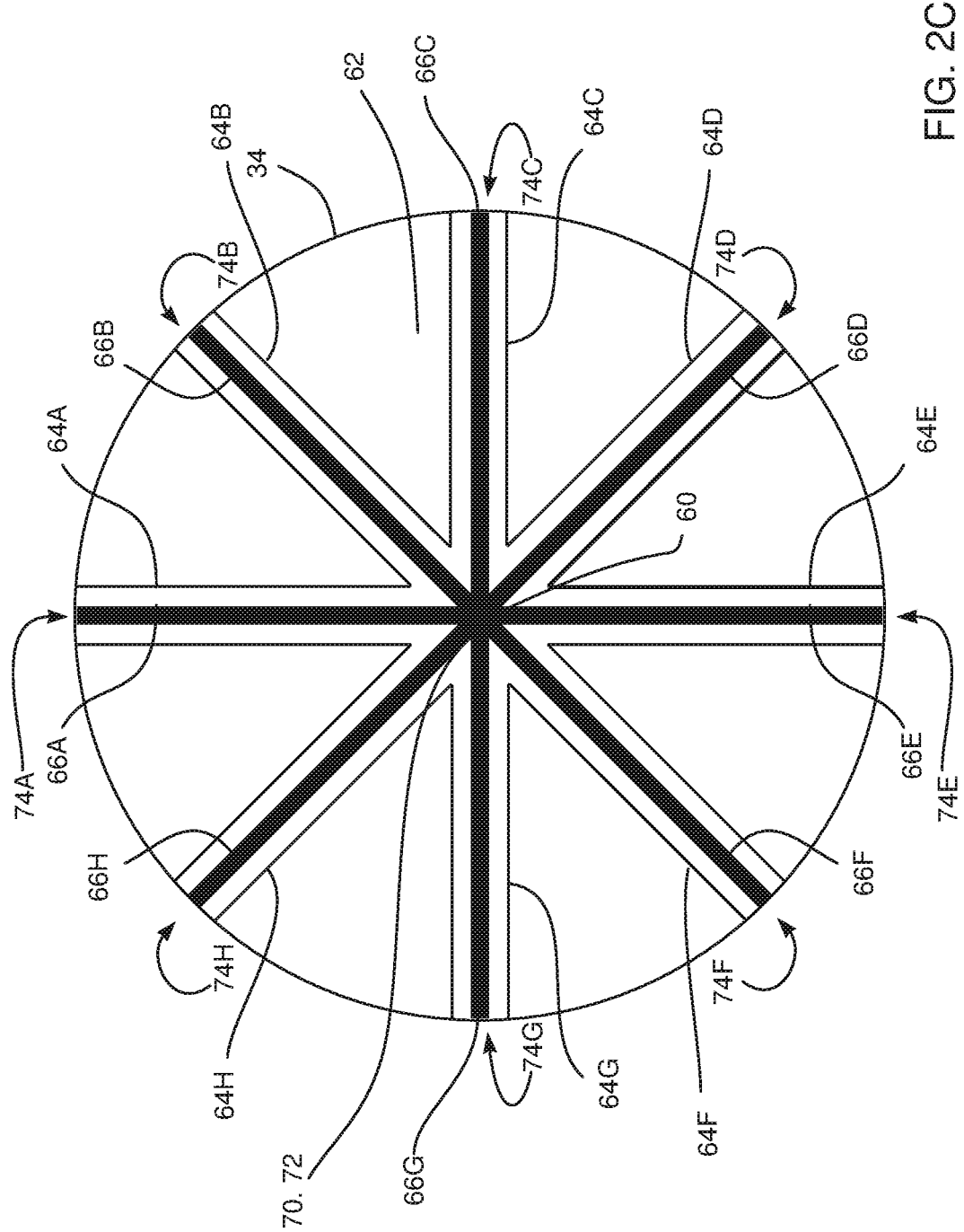

FIG. 1 is a schematic illustration of a medical system 20, comprising a medical probe 22 having a proximal end 23 and a distal end 26, according to an embodiment of the present invention. FIGS. 2A, 2B, and 2C are schematic illustrations of distal end 26 of probe 22, according to an embodiment of the present invention. System 20 may be based, for example, on the CARTO system produced by Biosense Webster Inc., of 33 Technology Drive, Irvine, CA 92618 USA, In embodiments described hereinbelow, medical probe 22 is used for diagnostic or therapeutic treatment, such as for mapping electrical potentials and/or for performing ablation procedures in a heart 28 of a patient 30. Alternatively, probe 22 may be used, mutatis mutandis, for other therapeutic and/or diagnostic purposes in the heart or in other body organs.

During a medical procedure using system 20, a medical professional 32 inserts medical probe 22 into a biocompatible sheath (not shown) that has been prepositioned in a lumen of the patient so that a balloon 34, described in more detail with reference to FIGS. 2A, 2B, and 2C, affixed to distal end 26 of the medical probe enters a chamber of heart 28.

System 20 is controlled by a system processor 46 which may be embodied as a single processor, or as a cooperatively networked or clustered set of processors. Processor 46 is typically a programmed digital computing device comprising a central processing unit (CPU), random access memory (RAM), non-volatile secondary storage, such as a hard drive or CD ROM drive, network interfaces, and/or peripheral devices. Program code, including software programs, and/or data are loaded into the RAM for execution and processing by the CPU and results are generated for display, output, transmittal, or storage, as is known in the art. Using its CPU and memories, processor 46 can be programmed to perform algorithms disclosed herein, using one or more modules, described hereinbelow, contained in a module bank 50 with which the processor communicates.

While for simplicity in the description herein processor 46 is assumed to be as described above, it will be understood that the scope of the invention includes a processor formed from any suitable integrated circuits, including, but not limited to, an ASIC (application specific integrated circuit), an FPGA (field-programmable gate array), an MCU (microcontroller unit), and a CPU.

In some embodiments processor 46 comprises real-time noise reduction circuitry 45, typically configured as an FPGA, followed by an analog-to-digital (A/D) signal conversion integrated circuit 47. The processor can pass the signals from A/D circuit 47 to modules described herein. The processor uses circuitry 45 and circuit 47, as well as features of the modules referred to above, in order to perform the algorithms.

Processor 46 is typically located in an operating console 24 of the system. Console 24 comprises controls 54 which are used by professional 32 to communicate with processor 46. Console 24 typically comprises a screen 56 upon which visual information generated by the processor, such as a map 48 of heart 28, may be presented to professional 32.

Console 24 is connected by a cable 36 to a location pad 25, typically situated beneath patient 30, comprising a plurality of fixed alternating magnetic field radiators. In one embodiment there are three sets of generally similar radiators 27A, 27B, and 27C, each radiator comprising three orthogonal coils which radiate respective magnetic fields at different frequencies, so that in this case there are nine separate fields that are radiated. Radiators 27A, 27B, and 27C, collectively herein termed radiators 27, are powered by a magnetic tracking module 52 in module bank 50, and radiate their magnetic fields into a volume including heart 28 and its surroundings.

In addition to powering radiators 27, module 52 is configured to record voltages developed by conductive elements on balloon 34, the voltages being created in response to the alternating magnetic fields, generated by radiators 27, that traverse the conductive elements. The voltage generation is described in more detail below, and, as is also described below, from the recorded voltages, processor 46 is able to derive the position and orientation of balloon 34.

FIGS. 2A and 2B are respectively schematic perspective illustrations of balloon 34 in a generally spherical form and in a generally ellipsoidal form, and FIG. 2C is a schematic illustration of balloon 34 as viewed from a point distal to the balloon. Balloon 34 is assumed to enclose a volume 38. FIG. 2A illustrates the balloon when fully inflated, and FIG. 2B illustrates the balloon in an at least partially inflated configuration. Typically, when partially or completed inflated, balloon 34 has a diameter of the order of about 20 mm to about 40 mm.

As stated above, balloon 34 is fixed to distal end 26, and the distal end defines a probe axis of symmetry 60 of the balloon when it is at least partially inflated. In order to convey the balloon through the prepositioned sheath referred to above, the balloon is initially in a deflated form, and in this form distal end 26 is inserted into heart 28. Once in place in heart 28, the balloon may be inflated, typically by injecting a fluid, such as saline solution, into the balloon. Once the procedure for which the balloon has been positioned in heart 28 has been completed, the balloon may be deflated and probe 22 (with the deflated balloon) may be withdrawn from patient 30.

So that the balloon may be deflated and inflated, balloon 34 is formed from a biocompatible flexible plastic material 62, and the material is fixed to a plurality of generally similar flexible splines 64A, 64B, ... 64H. Splines 64A, 64B, ... are generically referred to herein as splines 64 and the splines are typically distributed symmetrically about axis 60. In the disclosure and in the claims, a spline is assumed to be a long, narrow, thin strip or slat. Furthermore, because of its shape, a spline may be bent into a generally arcuate form.

While the number of splines 64 may be any convenient odd or even number of splines that is two or more, in the following description, by way of example, there are assumed to be eight splines 64A, 64B, ... 64H. In some embodiments splines 64 are internal to material 62, so that the splines act as ribs or spines covered by material 62. Alternatively, splines 64 are external to material 62, and the splines are attached by cement to the external surface of material 62 so as to support the material in place. Typically splines 64 are formed from flexible printed circuit (PC), a flexible wire such as nitinol, or a composition of such materials.

As is illustrated in FIGS. 2A and 2B, splines 64 surround, i.e., encompass, volume 38 enclosed by balloon 34.

For simplicity and clarity, in the following description, splines 64 are assumed to be external to material 62 and to be formed from flexible PC, and those having ordinary skill in the art will be able to adapt the description, mutatis mutandis, for the case of splines 64 being internal to the balloon material, and/or being formed from other materials referred to above.

Splines 64 typically comprise other elements, such as sensors, typically thermocouples or thermistors, to measure the temperature of heart tissue contacted by the splines, and electrodes. The electrodes may be used, inter alia, for radiofrequency (RF) ablation of the heart tissue, and/or for measuring and recording electrocardiogram (ECG) signals generated by the heart tissue. In some embodiments the other elements also comprise location sensors, typically coils, which provide signals in response to magnetic fields from radiators 27 traversing the sensors. Processor 46 may be configured to use such signals to find the location, i.e. the position and orientation, of the sensors. However, in some embodiments there are no such location sensors, since, as is described below, processor 46 uses signals from conductors in splines 64 to determine the position and the orientation of balloon 34.

Signals to and from such other elements are typically analyzed by, and/or generated by, processor 46 together with respective modules in module bank 50. For simplicity, such other elements and their respective modules are not shown in the figures.

Each spline 64A, 64B, . . . 64H comprises a respective conductor 66A, 66B, . . . 66H, the conductors being generically referred to herein as conductors 66. Conductors 66 may be formed on splines 64 by any convenient method, such as, but not limited to, by plating onto the splines. Thus splines 64 are also referred to herein as conductive splines 64. Conductors 66 have a common first termination 70 at a distal region 72 of the balloon, region 72 being beyond distal end 26 and being on axis 46, where the axis cuts material 62. In addition, conductors 66A, 66B, . . . 66H have respective second, separated, terminations 74A, 74B, . . . 74H, collectively referred to as 74. Signals from terminations 74A, 74B, . . . 74H, produced as described below, are conveyed by respective conductors 76A, 76B, . . . 76H to proximal end 23 of probe 22 and then to module 52, and processor 46 uses the module to analyze the signals, as is also described below.

In some embodiments one or more of conductors 66 may be configured to perform multiple functions, such as being able to act as the electrodes, and/or as at least one terminal of the temperature sensors, and/or as at least one terminal of the location sensors, all of which are referred to above.

When balloon 34 is at least partially inflated, each pair of conductors 66 is connected at common termination 70, terminates at respective different second terminations 74, and encloses a region defined by the specific pair of conductors 66 (i.e., defined by 66A, 66B, 66C . . . 66H). It will be understood that the specific pair of conductors 66 acts as a coil having a single turn. Thus, when the region enclosed by the single turn coil is traversed by alternating magnetic fields from radiators 27, Faraday's law of induction provides that an induced voltage is developed across the different second terminations 74 of the pair 66, and that the voltage depends on the area of the region enclosed, the intensity of the magnetic fields at the region, and the orientation of the region with respect to the magnetic fields.

Figure 3:
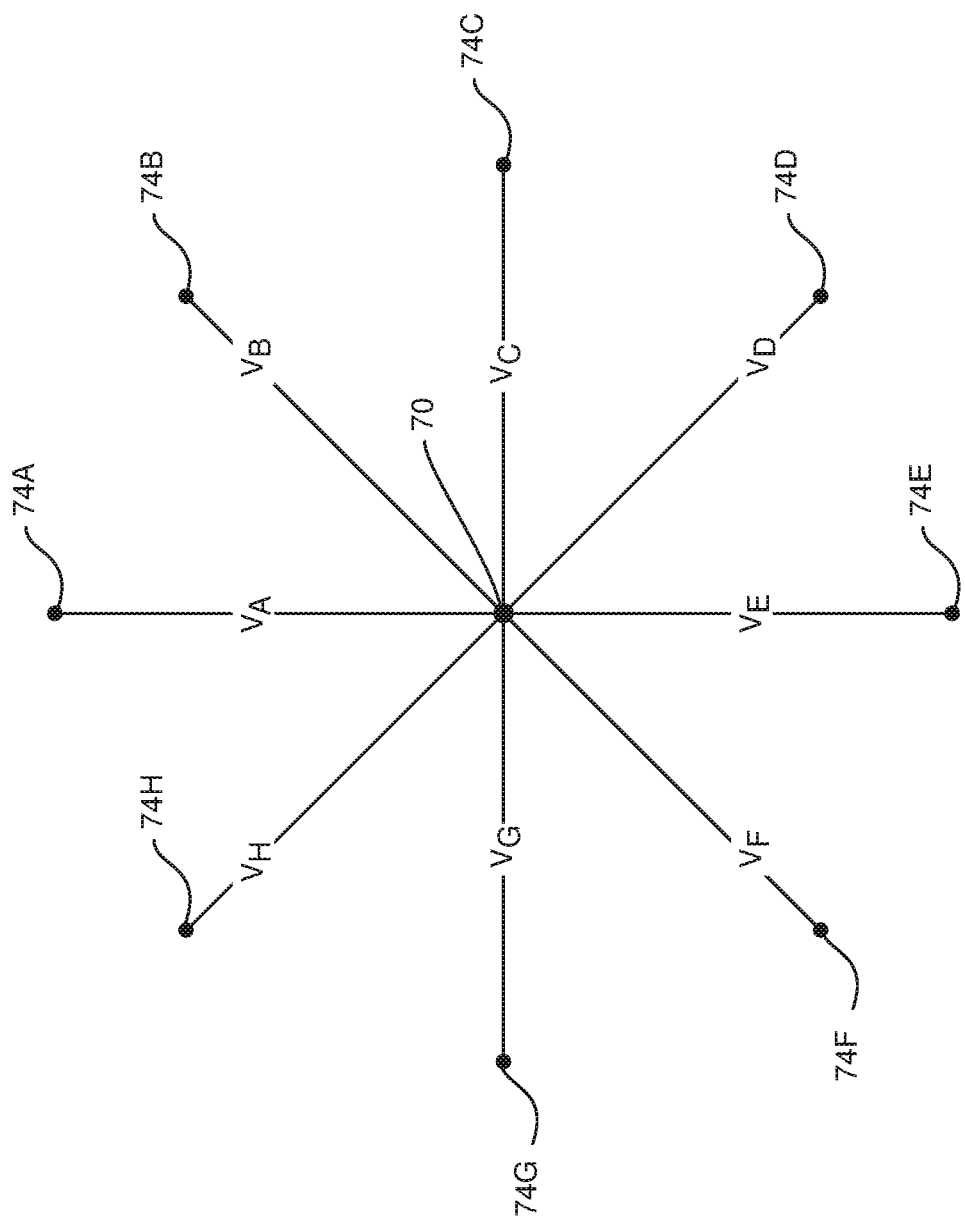
FIG. 3 illustrates voltages developed between different terminations of conductors on the probe and a common termination of the conductors, according to an embodiment of the present invention.

FIG. 3 illustrates the voltages developed between different terminations 74A, 74B, . . . 74H and common termination 70, according to an embodiment of the present invention. As is illustrated in the figure, voltages $V_A$, $V_B$, . . . $V_H$ may be considered to be generated between second terminations 74A, 74B, . . . 74H and common first termination 70 of conductors 66, and the measured voltage between any two second terminations is the sum of the two voltages assumed to be generated on the two conductors. For example, a measured voltage $V_{AC}$ between terminations 74A and 74C is assumed to be given by equation (1):

$$V_{AC} = V_A + V_C \quad (1)$$

Single axis sensors (SASs) having a coil with multiple turns are known in the art, and providing they are positioned in alternating magnetic fields that have been spatially mapped, it will be understood that the voltage developed across the coil can be used to find the position and orientation of the coil in the magnetic field. The Appendix below describes an algorithm for finding the position and orientation of an SAS in a mapped magnetic field, and those persons skilled in the art will be able to use the description of the algorithm, mutatis mutandis, to find the position and orientation of a single turn coil, such as a specific single turn coil defined by a pair of conductors 66. The algorithm is applicable since, inter alia, the overall area of a multiple turn SAS, typically having a diameter of the order of 1 mm, is of the same order as a single turn coil formed by a pair of conductors 66 on a balloon having a diameter of the order of 20 mm, so that the voltages formed by the multiple turn coil and the single turn coil (in the same magnetic field) are also of the same order.

For n conductors 66 (in splines 64), where n is an integer equal to or greater than 2, there are $$\binom{n}{2}$$

different possible pairs of conductors forming single turn coils generating $$\binom{n}{2}$$

respective voltages. Thus, for the 8 conductors (in their respective splines) considered here, there are 28 possible different single turn coils. This relationship would govern different single turn coils regardless of the number of n conductors. For example, where n=4, there are 6 possible different single turn coils; where n=6, there are 15 possible different single turn coils; where n=12, there are 66 possible different single turn coils and so on.

The voltage across each single turn coil gives the position and orientation of the coil, and the geometric relationships between the conductors, as well as the geometric relationships of the conductors to the balloon, are known or can be estimated. From the geometric relationships, and from the voltages developed by the 28 different single turn coils, processor 46 is able to estimate the position and orientation of volume 38 of balloon 34.

It will thus be understood that for n splines forming $$\binom{n}{2}$$

pairs of single turn coils, from the geometric relationships, and from the voltages developed by the $$\binom{n}{2}$$

coils, processor 46 is able to estimate the position and orientation of volume 38 of balloon 34.

Furthermore, rather than using all the $$\binom{n}{2}$$

pairs of single turn coils, processor 46 may be configured to estimate the position and orientation of volume 38 of balloon 34 using a selected subset of the coils.

Thus, in a disclosed embodiment, rather than analyzing the 28 different voltages generated by the set of eight conductors 66, processor 46 is configured to analyze the four sets of voltages generated by the subset of the eight conductors comprising four opposing pairs of conductors 66, (66A, 66E), (66B, 66F), (66C, 66G), (66D, 66H). I.e., the processor records and analyzes the voltages given by equations (2):

$$V_{AE} = V_A + V_E$$
$$V_{BF} = V_B + V_F$$
$$V_{CG} = V_C + V_G$$
$$V_{DH} = V_D + V_H \tag{2}$$

Each opposing pair of conductors 66 (e.g., 66A and 66E forming one pair) in general forms a planar ellipse. (In the case of full inflation of balloon 34 the ellipse is approximately circular with an approximately unity ellipticity.) Furthermore, the centers of each of the four ellipses are approximately the same, corresponding to the center of volume 38. Because of the symmetry of splines 64 each of the four ellipses typically has substantially the same ellipticity, so that balloon 34 is effectively an ellipsoid of revolution around axis 60. Because, by virtue of the known construction of splines 64 on balloon 34, the orientation of the four ellipses with respect to each other is known, these orientations may be used to calculate an orientation of the balloon and a magnitude of its enclosed volume. By estimating the location of the balloon, i.e. its position and orientation, as well as its volume, the processor is able to provide a virtual representation of the actual size of the physical balloon and its actual location relative to the structures of the heart in a medical procedure.

Figure 4:
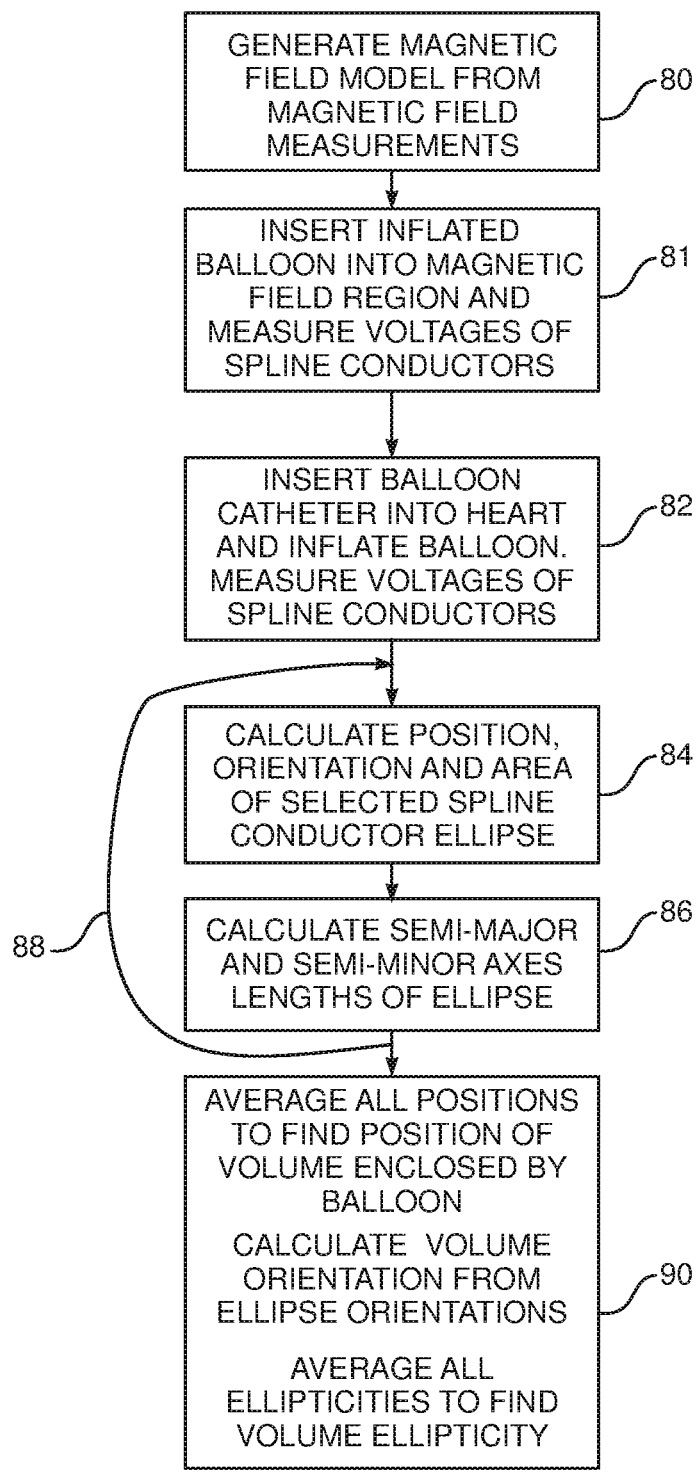
FIG. 4 is a flowchart of steps of a balloon catheter algorithm implemented by a processor for a balloon, according to an embodiment of the present invention.

FIG. 4 is a flowchart of steps of a balloon catheter algorithm implemented by processor 46 for balloon 34, according to an embodiment of the present invention. The algorithm assumes that voltages of the four pairs of opposing conductors 66 of the disclosed embodiment described above, describing the four ellipses of the balloon, are measured. From the measured voltages, processor 46 finds the position and orientation of volume 38.

In a generation step 80, a magnetic field model $\overrightarrow{B_{model}}(x,y,z)$ is generated from magnetic field measurements made in a region (that will surround heart 28 in a subsequent step of the algorithm) by a magnetic sampling detector scanned within the region at predefined points. The magnetic fields in the region are provided by the nine radiators 27, which are typically configured to transmit simultaneously at nine different frequencies. The magnetic field model, which provides a correspondence between a position (x,y,z) and the nine measured magnetic fields at the position, is fitted to the magnetic field measurements at the predefined points.

In a calibration step 81, balloon 34 is inflated, typically so that the balloon is approximately spherical, and the area of each of the four ellipses is measured. If the balloon is approximately spherical, then the ellipses are approximately circles, and the area of each ellipse is the same and is known from the balloon diameter. The area of each ellipse is herein assumed to be Area$_{cal}$.

The inflated balloon is inserted into a known magnetic field $\Phi$, typically produced by a Helmholtz coil, and voltages Meas$_{cal}$ of each of the four ellipses are measured and recorded by processor 46. It will be understood that there are nine voltages for each ellipse (from the nine radiators 27). From Faraday's law of induction the voltage is directly proportional to the product of Area$_{cal}$ and a projection $\Phi_p$ of the magnetic field $\Phi$ onto the ellipse, so that $$\text{Meas}_{cal} = k \text{Area}_{cal} \Phi_p \tag{3}$$

where k is a constant of proportionality.

The processor stores the value of k for use in an ellipticity calculation step 86.

In a catheter insertion step 82, patient 30 is moved so that their heart is in the magnetic field region, and probe 22 is inserted into the patient so that balloon 34 enters the heart of the patient. The balloon is then inflated, and voltages Meas generated at second terminations 74A, 74B, . . . 74H, of spline conductors 66, are measured and recorded by processor 46 using module 52. For each ellipse formed by opposing conductors 66, there are nine different voltages generated by the nine magnetic fields from radiators 27.

In a location calculation step 84, processor 46 calculates the position and orientation of a specific ellipse, using the nine voltages measured and the magnetic field model $\overrightarrow{B_{model}}(x,y,z)$ derived in step 80. Methods for calculating the position and orientation of a coil in a plurality of alternating magnetic fields are known in the art, and are used, for example, in the CARTO system referred to above. A method for calculating the position and orientation of a coil in a plurality of alternating magnetic fields is described in U.S. Pat. No. 8,818,486 to Montag, which is incorporated herein by reference. In addition, a method for calculating the position and orientation of a coil in a plurality of alternating magnetic fields is described in the Appendix below. The two latter methods are based on minimization. In step 84 the processor may also calculate the area of the specific ellipse, typically using a method as described in the Appendix below. Alternatively or additionally, the area may be calculated as described below in step 86.

In ellipticity calculation step 86, processor 46 calculates the ellipticity of the specific ellipse, i.e., the ratio between the semi-major axis length a and the semi-minor axis length b using magnitudes of the nine voltages Meas measured in step 82. Values of the magnitudes enable the processor to estimate an area A of the specific ellipse, as is explained below.

The ellipses of calibration step 81 are typically deformed in step 82, having an unknown area A. However, as stated above, the voltages produced by any given ellipse are directly proportional to the area of the ellipse and to the projection of the magnetic field onto the ellipse, so that using equation (3) the following equation holds:

$$\text{Meas} = kA[(v_x, v_y, v_z) \cdot \overrightarrow{B_{model}}(x,y,z)] \tag{4}$$

where $(v_x, v_y, v_z)$ is a direction vector subject to the constraint that $\|(v_x, v_y, v_z)\| = 1$.

In step 86 processor 46 uses equation (4), and the value of constant k derived in step 81, to estimate the area A of each ellipse. In equation (4) there are six unknowns; however, since there are nine independent radiators 27, there is more than sufficient information for processor 46 to use equation (4) to estimate a given ellipse area.

Equations (5) and (6) below are equations respectively relating the area A of an ellipse to a and b, and a perimeter p of the ellipse to a and b. The value of perimeter p is the total length of the conductors 66 forming the ellipse, and this value is known.

$$A = \pi a b \quad (5)$$

$$p \approx \pi[3(a+b) - \sqrt{(3a+b)(a+3b)}] \quad (6)$$

Using the values of A and p, processor 46 solves equations (5) and (6) for a and b, and thus the ellipticity of the specific ellipse.

As indicated by an arrow 88, the processor repeats the calculations of steps 84 and 86 for all the four ellipses generated by opposing conductors 66.

In a concluding step 90 of the algorithm, the processor averages the four positions of the ellipses to find the position of volume 38. The processor also finds an orientation of volume 38 from the four ellipse orientations. An average of the ellipticities of the ellipses gives a value for the ellipticity of the ellipsoid of revolution of volume 38.

Since volume 38 is an ellipsoid of revolution, a magnitude V of this volume, i.e. the volume enclosed by balloon 34, is given by equation (7):

$$V = \frac{4\pi}{3} a b^2 \quad (7)$$

In a disclosed embodiment, using the position, orientation, and magnitude of volume 38 as determined above, the processor may present in step 90, on map 48 of the heart (FIG. 1), a virtual representation of the actual size of balloon 34 and the balloon's actual location relative to the structures of the heart. The presentation may be implemented during a medical procedure.

Alternatively or additionally, the processor may present on screen 56 a numerical value of magnitude V. Professional 32 may estimate from the numerical value, and/or from the virtual representation, if balloon 34 has been underinflated or overinflated.

While the description above for the flowchart of FIG. 4 considers splines forming four pairs of coils, those persons skilled in the art will be able to adapt the description, mutatis mutandis, for other possible numbers of pairs of coils, and all such possible numbers are considered to be within the scope of the present invention.

Figure 5:
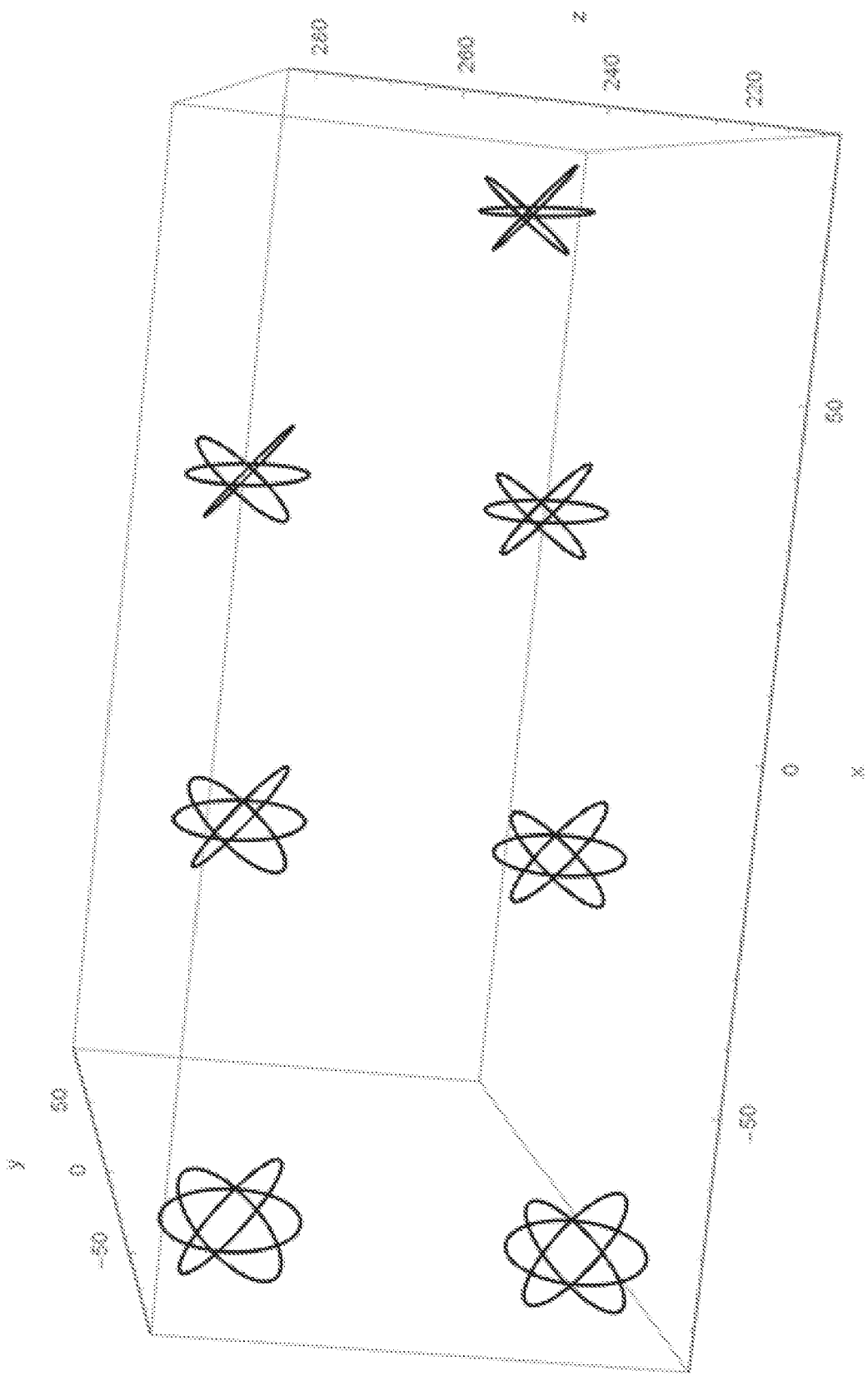
FIG. 5 illustrates experimental results, using a system similar to the medical system of FIG. 1, according to an embodiment of the present invention.

FIG. 5 illustrates experimental results obtained by the inventors, using a system similar to system 20, according to an embodiment of the present invention. The results are for the four ellipse systems described above with reference to FIGS. 3 and 4. The figure shows, for seven selected positions of volume 38 enclosed by balloon 34, three of the four ellipses that processor 46 calculates at each of the seven positions.

APPENDIX

Figure 6:
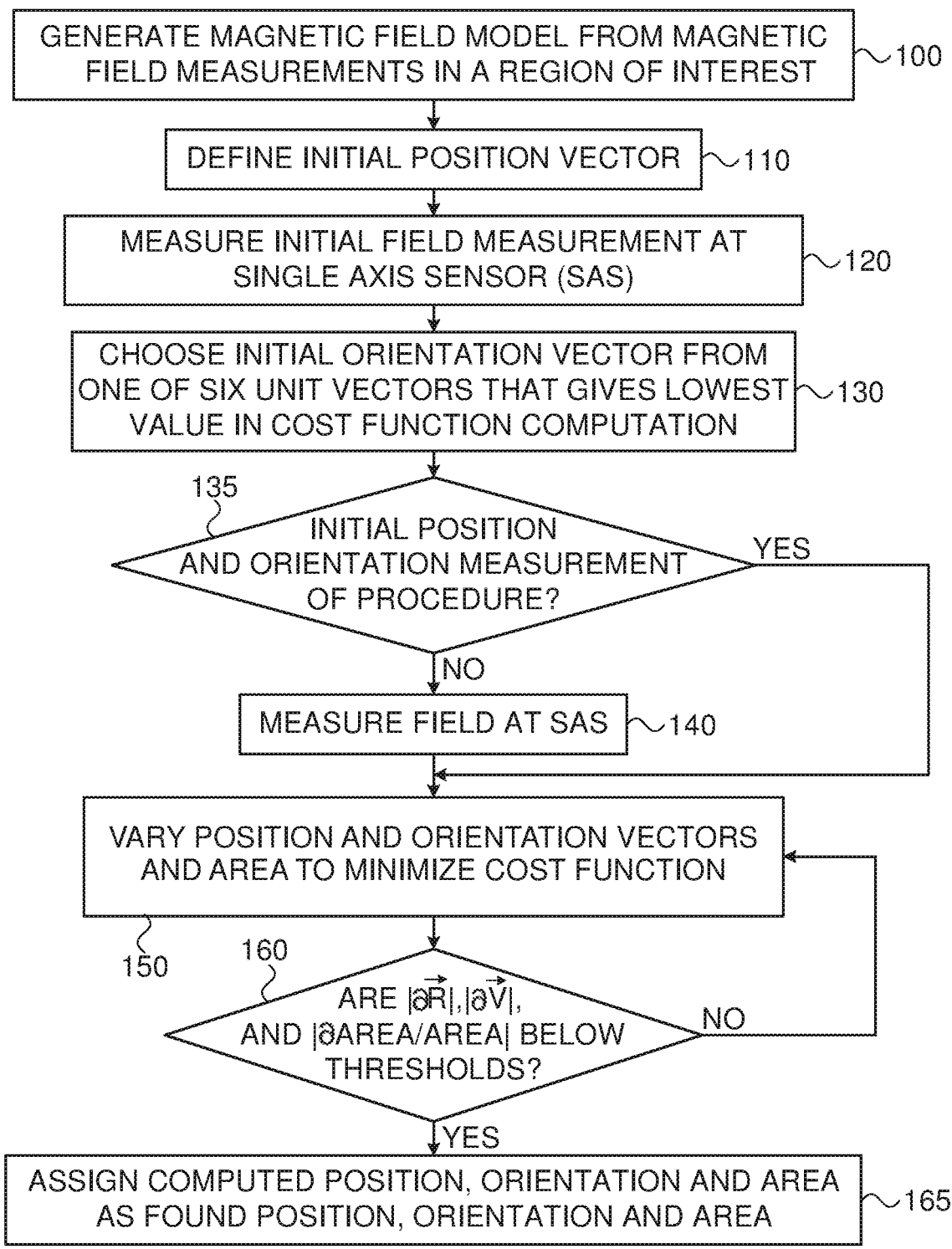
FIG. 6 is a flowchart describing steps of a position and orientation algorithm for tracking a single axis sensor of a catheter, according to an embodiment of the present invention.

FIG. 6 is a flowchart describing steps of a position and orientation (P&O) algorithm for tracking a single axis sensor (SAS) of a catheter, according to an embodiment of the present invention. The flowchart assumes that the SAS comprises one or more turns of a coil, and that the SAS is in a region of interest (ROI) irradiated by i alternating magnetic fields generated by i respective magnetic field generators, where i is a positive integer. In the following description i=9, corresponding to radiators 27 described above, and the ROI may be assumed to comprise a region containing heart 28. The P&O algorithm is assumed to be implemented by processor 46 using magnetic tracking module 52.

In a generation step 100, a magnetic field model $\vec{B}_{model}(x,y,z)$, substantially the same as step 80 of the balloon catheter algorithm, is generated from magnetic field measurements made in the ROI by a magnetic sampling detector scanned within the ROI at predefined points. The magnetic field model is fitted to the magnetic field measurements at the predefined points.

At a definition step 110, an initial position vector is defined by arbitrarily assigning an initial SAS position vector $\vec{r} = (x,y,z)$ of the distal tip of the catheter, at a point such as a center of the ROI.

In a first measurement step 120, i initial magnetic field measurements, $meas_i$, are measured at the single axis sensor. The field measurements are received by module 52 and relayed to processor 46.

In a choosing step 130, an initial orientation vector is chosen from one of six unit vectors, e.g., ((1,0,0), (−1,0,0), (0,1,0), (0,−1,0), (0,0,1), (0,0,1)). Processor 46 computes six cost functions cost using equations (A)-(C) below.

$$\Delta Meas_i = Mest_i - meas_i \quad (A)$$

$$cost = \Sigma_{i=1}^{10} \Delta Meas_i^2 \quad (B)$$

where $\Delta Meas_{10}$ is a penalty function given by $$\Delta Meas_{10} = constraintWeight(v_x^2 + v_y^2 + v_z^2 = -1) \quad (C)$$

$v_x$, $v_y$, $V_z$, are components of an SAS orientation vector $\vec{v} = (v_x, v_y, v_z)$, $$Mest_i = \frac{Area}{Area_{cal}}(v_x, v_y, v_z) \cdot B_{model}(x, y, z)_i$$

Area is an actual area of the SAS,
$Area_{cal}$ is the calibrated area of the SAS,
and constraintWeight is a constant typically with a value of constraintWeight=0.05.

In step 130 processor 46 uses the initial field measurement from step 120, the six unit vectors, and the initial position vector defined in step 110. The initial orientation vector chosen is the one that gives the lowest value of cost in six cost function computations of equation (B).

In a first decision step 135, if this is the initial position and orientation measurement, processor 46 bypasses a second measurement step 140, since the fields were already measured in step 120. If this is not the initial measurement, fields $meas_i$ are measured at the single axis sensor in second measurement step 140.

In a varying step 150 and a second decision step 160, processor 46 initiates an iteration loop after step 140 to minimize the cost function value cost. In step 150 SAS position vector $\vec{r} = (x,y,z)$ and SAS orientation vector $\vec{v} = (v_x, v_y, v_z)$ are varied to reduce the cost function.

While in the iteration loop, not only is the cost function reduced, typically monotonically, but processor 46 also computes the seven differential variables ($\partial x$, $\partial y$, $\partial z$, $\partial v_x$, $\partial v_y$, $\partial v_z$, $\partial$Area) using a Levenberg-Marquardt (L-M) variation of the Gauss-Newton (G-N) optimization method, according to equation (D):

$$\begin{pmatrix} \partial x \\ \partial y \\ \partial z \\ \partial v_x \\ \partial v_y \\ \partial v_z \\ \partial \text{Area} \end{pmatrix} = -(J^T J + \lambda \text{diag}(J))^{-1} J^T \Delta Meas \quad (D)$$

where J is the Jacobian matrix, $j^T$ is the transpose of J, diag(J) is a diagonal matrix whose elements are the diagonal elements of J, and $\lambda$ is a non-negative scalar parameter, which is typically approximately 0.001, and which shrinks by a factor of 10 in every iteration. $\Delta$Meas in equation (D) is a 10×1 matrix, which comprises nine terms from the nine radiators 27 and one penalty function term from equation (C).

The seven differentials ($\partial x$, $\partial y$, $\partial z$, $\partial v_x$, $\partial v_y$, $\partial v_z$, $\partial$Area) computed iteratively from equation (D) represent the differential changes of the components of position vector r=(x,y,z), the differential changes of the components of orientation vector v=($v_x, v_y, v_z$), and the change in area between successive iteration loop cycles.

Using the seven differentials, processor 46 calculates a change in the position vector $|\partial \vec{r}| = \sqrt{(\partial x)^2 + (\partial y)^2 + (\partial z)^2}$, a change in the orientation vector $|\partial \vec{v}| = \sqrt{(\partial v_x)^2 + (\partial v_y)^2 + (\partial v_z)^2}$, and a change in the area $\partial$Area between iteration loop cycles.

In a second decision step 160, when $|\partial \vec{r}|$, $|\partial \vec{v}|$, and $|\partial$Area$|$/Area are not below a predefined threshold, typically 0.002, the iteration loop continues with varying step 150. If $|\partial \vec{r}|$, $|\partial \vec{v}|$, and $|\partial$Area$|$/Area are below the predefined threshold, processor 46 assigns the computed position, orientation, and area as the found position, orientation, and area in an assignment step 165, i.e. the measured position and orientation vector, and the area, of the SAS.

While the description above has assumed splines forming a balloon catheter positioned in a heart, it will be understood that embodiments of the present invention may be implemented for splines forming a basket catheter. It will also be understood that embodiments of the present invention may be used for procedures on organs other than the heart, such as sinuplasty procedures.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art.

The invention claimed is:

1. Apparatus, comprising:
   a probe having a proximal end and a distal end, the probe being configured to be inserted into an organ of a human patient and defining a probe axis;
   at least two conductors positioned on the probe at the distal end;
   at least two flexible conductive splines, each conductive spline having a first termination and a second termination, each of the first terminations being electrically connected together at a region on the probe axis beyond the distal end of the probe and forming one or more pairs, each pair of the one or more pairs comprising two flexible conductive splines of the at least two flexible conductive splines such that each pair of the one or more pairs forms a respective single turn coil comprising the two flexible conductive splines, each second termination being electrically connected to a respective one of the at least two conductors, the at least two flexible conductive splines being configured to bend into respective arcuate forms that encompass a volume; and
   a processor configured:
   to receive one or more voltages induced on each respective single turn coil via the at least two conductors, and
   to calculate a position and orientation of the volume in response to the one or more received voltages.

2. The apparatus according to claim 1, wherein the at least two flexible conductive splines are attached to flexible material forming a balloon catheter.

3. The apparatus according to claim 1, wherein the probe and the at least two flexible conductive splines form a basket catheter.

4. The apparatus according to claim 1, wherein the processor is configured to calculate an ellipticity of the volume in response to the received one or more voltages.

5. The apparatus according to claim 1, further comprising:
   at least one magnetic field radiator which generates an alternating magnetic field traversing the volume encompassed by the at least two flexible conductive splines so as to generate the received one or more voltages.

6. The apparatus according to claim 1, wherein the at least two flexible conductive splines comprise an even number of flexible conductive splines, and wherein the processor is configured to calculate respective centers and orientations of opposing pairs of the one or more pairs, and to derive the position and orientation of the volume from the respective centers and orientations.

7. The apparatus according to claim 1, wherein the at least two conductors and the at least two flexible conductive splines are distributed symmetrically about the probe axis.

8. The apparatus according to claim 1, wherein the at least two conductors and the at least two flexible conductive splines are equal in number.

9. The apparatus according to claim 1, wherein the at least two flexible conductive splines comprise n splines, where n is an integer greater than or equal to three, and wherein the processor is configured to receive a subset of $$\binom{n}{2}$$

voltages induced in respective $$\binom{n}{2}$$

different pairs of of the one or more pairs, and to calculate the position and orientation of the volume in response to the received subset.

10. The apparatus according to claim 1, wherein the at least two flexible conductive splines comprise n splines, where n is an integer greater than or equal to two, and wherein the processor is configured to receive $$\binom{n}{2}$$

voltages induced in respective $$\binom{n}{2}$$

different pairs of of the one or more pairs, and to calculate the position and orientation of the volume in response to the received $$\binom{n}{2}$$

voltages.

11. The apparatus according to claim 1, wherein the processor is configured to calculate a magnitude of the volume in response to the received one or more voltages.

12. The apparatus according to claim 11, wherein the at least two flexible conductive splines are attached to flexible material forming a balloon catheter, the apparatus further comprising a screen, and wherein the processor is configured to present, on the screen, a virtual representation of the balloon catheter in response to the position, the orientation, and the magnitude of the volume.

13. A method, comprising:
configuring a probe, having a proximal end and a distal end, to be inserted into an organ of a human patient, the probe defining a probe axis;
positioning at least two conductors on the probe at the distal end thereof;
providing at least two flexible conductive splines, each flexible conductive spline of the at least two flexible conductive splines having a first termination and a second termination;
electrically connecting the first terminations at a region on the probe axis beyond the distal end of the probe to form one or more pairs, each pair comprising two flexible conductive splines of the at least two flexible conductive splines such that each pair forms a respective single turn coil comprising the two flexible conductive splines;
electrically connecting each second termination to a respective one of the at least two conductors;
bending the splines into respective arcuate forms that encompass a volume; and
receiving voltages induced on each respective single turn coil via the at least two conductors, and calculating a position and orientation of the volume in response to the received one or more voltages.

14. The method according to claim 13, wherein the at least two flexible conductive splines are attached to flexible material forming a balloon catheter.

15. The method according to claim 13, wherein the probe and the at least two flexible conductive splines form a basket catheter.

16. The method according to claim 13, and comprising calculating an ellipticity of the volume in response to the received one or more voltages.

17. The method according to claim 13, and comprising generating an alternating magnetic field traversing the volume encompassed by the at least two flexible conductive splines so as to generate the received one or more voltages.

18. The method according to claim 13, wherein the at least two flexible conductive splines comprise an even number of splines, the method comprising calculating respective centers and orientations of opposing pairs of the one or more pairs, and deriving the position and orientation of the volume from the respective centers and orientations.

19. The method according to claim 13, and comprising distributing the at least two conductors and the at least two flexible conductive splines symmetrically about the probe axis.

20. The method according to claim 13, wherein the at least two conductors and the at least two flexible conductive splines are equal in number.

21. The method according to claim 13, wherein the at least two flexible conductive splines comprise n splines, where n is an integer greater than or equal to three, the method comprising receiving a subset of $$\binom{n}{2}$$

voltages induced in respective $$\binom{n}{2}$$

different pairs of the one or more pairs, and calculating the position and orientation of the volume in response to the received subset.

22. The method according to claim 13, wherein the at least two flexible conductive splines comprise n splines, where n is an integer greater than or equal to two, the method comprising receiving $$\binom{n}{2}$$

voltages induced in respective $$\binom{n}{2}$$

different pairs of the one or more pairs, and calculating the position and orientation of the volume in response to the received $$\binom{n}{2}$$

voltages.

23. The method according to claim 13, and comprising calculating a magnitude of the volume in response to the received one or more voltages.

24. The method according to claim 23, wherein the at least two flexible conductive splines are attached to flexible material forming a balloon catheter, the method further comprising presenting, on a screen, a virtual representation of the balloon catheter in response to the position, the orientation, and the magnitude of the volume.

* * * * *